(12) United States Patent
Stone et al.

(10) Patent No.: US 9,981,418 B2
(45) Date of Patent: May 29, 2018

(54) PROCESS FOR MAKING A MICRO-TEXTURED WEB

(71) Applicant: The Procter & Gamble Company, Cincinnati, OH (US)

(72) Inventors: Keith Joseph Stone, Fairfield, OH (US); Richard George Coe, Cincinnati, OH (US); Mathias Johannes Hilpert, Mason, OH (US); James William Busch, Maineville, OH (US); Kasey Marie Gust, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 440 days.

(21) Appl. No.: 14/681,125

(22) Filed: Apr. 8, 2015

(65) Prior Publication Data
US 2015/0209999 A1     Jul. 30, 2015

Related U.S. Application Data

(63) Continuation of application No. 13/094,477, filed on Apr. 26, 2011, now Pat. No. 9,044,353.

(51) Int. Cl.
| | | |
|---|---|---|
| *B29C 55/18* | (2006.01) | |
| *A61F 13/15* | (2006.01) | |
| *B29L 7/00* | (2006.01) | |
| *B29L 9/00* | (2006.01) | |
| *B29L 31/34* | (2006.01) | |

(Continued)

(52) U.S. Cl.
CPC ........ *B29C 55/18* (2013.01); *A61F 13/15731* (2013.01); *B29L 2007/00* (2013.01); *B29L 2009/00* (2013.01); *B29L 2031/3406* (2013.01); *B29L 2031/4878* (2013.01); *B29L 2031/7128* (2013.01); *B29L 2031/753* (2013.01)

(58) Field of Classification Search
CPC ... B29C 55/18; B29C 59/04; B29C 2059/023; B29C 66/7294; B29C 66/81433; B29C 66/83411; B31F 2201/0733; B31F 2201/0774; B32B 5/022
See application file for complete search history.

(56) References Cited

U.S. PATENT DOCUMENTS

| | | |
|---|---|---|
| 2,068,456 A | 1/1937 | Hooper |
| 2,275,425 A | 3/1942 | Grabec |

(Continued)

FOREIGN PATENT DOCUMENTS

| | | |
|---|---|---|
| EP | 0509012 | 7/1995 |
| EP | 0955159 | 11/1999 |

(Continued)

*Primary Examiner* — Stella K Yi
(74) *Attorney, Agent, or Firm* — George H. Leal

(57) ABSTRACT

Processes for making micro-textured webs are disclosed. The present process includes the steps of providing a precursor web; providing a first pair of mated forming members including a first forming member and a second forming member forming a first deformation zone therebetween; moving the precursor web through the first deformation zone forming a first plurality of structures; providing a second pair of mated forming members including a third forming member and a fourth forming member forming a second deformation zone therebetween; moving the precursor web through the second deformation zone forming a second plurality of structures, and wherein the first plurality of structures is different than the second plurality of structures.

20 Claims, 26 Drawing Sheets

(51) Int. Cl.
    *B29L 31/48*       (2006.01)
    *B29L 31/00*       (2006.01)

(56)             References Cited

U.S. PATENT DOCUMENTS

| | | | |
|---|---|---|---|
| 2,404,758 A | 7/1946 | Teague |
| 2,633,441 A | 3/1953 | Buttress |
| 2,748,863 A | 6/1956 | Benton |
| 2,924,863 A | 2/1960 | Chavannes |
| 3,073,304 A | 1/1963 | Schaar |
| 3,081,500 A | 3/1963 | Griswold et al. |
| 3,081,512 A | 3/1963 | Griswold |
| 3,137,893 A | 6/1964 | Gelpke |
| 3,355,974 A | 12/1967 | Carmichael |
| 3,496,259 A | 2/1970 | Guenther |
| 3,511,740 A | 5/1970 | Sanders |
| 3,542,634 A | 11/1970 | Such |
| 3,566,726 A | 3/1971 | Politis |
| 3,579,763 A | 5/1971 | Sommer |
| 3,681,182 A | 8/1972 | Kalwaites |
| 3,681,183 A | 8/1972 | Kalwaites |
| 3,684,284 A | 8/1972 | Tranfield |
| 3,695,270 A | 10/1972 | Zdenek |
| 3,718,059 A | 2/1973 | Clayton |
| 3,760,671 A | 9/1973 | Jenkins |
| 3,881,987 A | 5/1975 | Benz |
| 3,911,187 A | 10/1975 | Raley |
| 3,949,127 A | 4/1976 | Ostermeier |
| 3,965,906 A | 6/1976 | Karami |
| 4,035,881 A | 7/1977 | Zocher |
| 4,042,453 A | 8/1977 | Conway |
| 4,135,021 A | 1/1979 | Patchell |
| 4,276,336 A | 6/1981 | Sabee |
| 4,379,799 A | 4/1983 | Holmes |
| 4,397,644 A | 8/1983 | Matthews |
| 4,463,045 A | 7/1984 | Ahr et al. |
| 4,465,726 A | 8/1984 | Holmes |
| 4,469,734 A | 9/1984 | Minto |
| 4,588,630 A | 5/1986 | Shimalla |
| 4,695,422 A | 9/1987 | Curro et al. |
| 4,741,941 A | 5/1988 | Englebert et al. |
| 4,758,297 A | 7/1988 | Calligarich |
| 4,781,962 A | 11/1988 | Zanarripa |
| 4,798,604 A | 1/1989 | Carter |
| 4,820,294 A | 4/1989 | Morris |
| 4,840,829 A | 6/1989 | Suzuki |
| 4,859,519 A | 8/1989 | Cabe |
| 4,886,632 A | 12/1989 | Van Iten et al. |
| 4,935,087 A | 6/1990 | Gilman |
| 4,953,270 A | 9/1990 | Gilpatrick |
| 5,019,062 A | 5/1991 | Ryan et al. |
| 5,062,418 A | 11/1991 | Dyer et al. |
| 5,144,730 A | 9/1992 | Dilo |
| 5,158,819 A | 10/1992 | Goodman, Jr. et al. |
| 5,165,979 A | 11/1992 | Watkins et al. |
| 5,171,238 A | 12/1992 | Kajander |
| 5,180,620 A | 1/1993 | Mende |
| 5,188,625 A | 2/1993 | Van Iten et al. |
| 5,223,319 A | 6/1993 | Cotton et al. |
| 5,242,632 A | 9/1993 | Mende |
| 5,382,245 A | 1/1995 | Thomspon et al. |
| 5,383,870 A | 1/1995 | Takai et al. |
| 5,387,209 A | 2/1995 | Yamamoto et al. |
| 5,414,914 A | 5/1995 | Suzuki et al. |
| 5,415,640 A | 5/1995 | Kirby et al. |
| 5,429,854 A | 7/1995 | Currie et al. |
| 5,437,653 A | 8/1995 | Gilman et al. |
| 5,470,326 A | 11/1995 | Dabi et al. |
| 5,508,080 A | 4/1996 | Sorimachi et al. |
| 5,518,801 A | 5/1996 | Chappell et al. |
| 5,533,991 A | 7/1996 | Kirby et al. |
| 5,554,145 A | 9/1996 | Roe et al. |
| 5,560,794 A | 10/1996 | Currie et al. |
| 5,567,501 A | 10/1996 | Srinivasan et al. |
| D375,844 S | 11/1996 | Edwards et al. |
| 5,573,719 A | 11/1996 | Fitting |
| 5,575,874 A | 11/1996 | Griesbach, III et al. |
| 5,580,418 A | 12/1996 | Alikhan |
| 5,599,420 A | 2/1997 | Yeo et al. |
| 5,624,427 A | 4/1997 | Bergman et al. |
| 5,626,571 A | 5/1997 | Young et al. |
| 5,628,097 A | 5/1997 | Benson et al. |
| 5,648,142 A | 7/1997 | Phillips |
| 5,656,119 A | 8/1997 | Srinivasan et al. |
| 5,658,639 A | 8/1997 | Curro et al. |
| 5,667,619 A | 9/1997 | Alikhan |
| 5,667,625 A | 9/1997 | Alikhan |
| 5,691,035 A | 11/1997 | Chappell et al. |
| 5,700,255 A | 12/1997 | Curro et al. |
| 5,704,101 A | 1/1998 | Majors et al. |
| 5,709,829 A | 1/1998 | Giacometti |
| 5,714,107 A | 2/1998 | Levy |
| 5,723,087 A | 3/1998 | Chappell et al. |
| 5,743,776 A | 4/1998 | Igaue et al. |
| 5,804,021 A | 9/1998 | Abuto et al. |
| 5,814,389 A | 9/1998 | Giacometti |
| 5,817,394 A | 10/1998 | Alikhan et al. |
| 5,841,107 A | 11/1998 | Riva |
| 5,858,504 A | 1/1999 | Fitting |
| 5,879,494 A | 3/1999 | Hoff et al. |
| 5,891,544 A | 4/1999 | Chappell et al. |
| 5,895,623 A | 4/1999 | Trokhan et al. |
| 5,914,084 A | 6/1999 | Benson et al. |
| 5,916,661 A | 6/1999 | Benson et al. |
| 5,919,177 A | 7/1999 | Georger et al. |
| 5,925,026 A | 7/1999 | Arteman et al. |
| 5,964,742 A | 10/1999 | McCormack et al. |
| 5,968,029 A | 10/1999 | Chappell et al. |
| 5,986,167 A | 11/1999 | Arteman et al. |
| 5,993,432 A | 11/1999 | Lodge et al. |
| 6,007,468 A | 12/1999 | Giacometti |
| 6,025,050 A | 2/2000 | Srinivasan et al. |
| 6,027,483 A | 2/2000 | Chappell et al. |
| 6,039,555 A | 3/2000 | Tsuji et al. |
| 6,096,016 A | 8/2000 | Tsuji et al. |
| 6,114,263 A | 9/2000 | Benson et al. |
| 6,117,524 A | 9/2000 | Hisanaka et al. |
| 6,120,718 A | 9/2000 | Kotek et al. |
| 6,129,801 A | 10/2000 | Benson et al. |
| 6,155,083 A | 12/2000 | Goeser et al. |
| 6,168,849 B1 | 1/2001 | Braverman et al. |
| 6,176,954 B1 | 1/2001 | Tsuji et al. |
| 6,247,914 B1 | 6/2001 | Lindquist et al. |
| 6,264,872 B1 | 6/2001 | Majors et al. |
| D444,631 S | 7/2001 | Woodbridge et al. |
| 6,287,407 B1 | 9/2001 | Stein et al. |
| 6,383,431 B1 | 5/2002 | Dobrin et al. |
| 6,395,122 B1 | 5/2002 | Hisanaka et al. |
| 6,395,211 B1 | 5/2002 | Dettmer et al. |
| 6,398,895 B1 | 6/2002 | Stein et al. |
| 6,410,823 B1 | 6/2002 | Daley et al. |
| 6,420,625 B1 | 7/2002 | Jones et al. |
| 6,423,884 B1 | 7/2002 | Oehmen et al. |
| 6,451,718 B1 | 9/2002 | Yamada et al. |
| 6,452,064 B1 | 9/2002 | Thoren et al. |
| 6,458,447 B1 | 10/2002 | Cabell et al. |
| 6,479,130 B1 | 11/2002 | Takai et al. |
| D466,702 S | 12/2002 | Carson et al. |
| 6,506,329 B1 | 1/2003 | Curro et al. |
| 6,537,936 B1 | 3/2003 | Busam et al. |
| 6,620,485 B1 | 9/2003 | Benson et al. |
| 6,632,504 B1 | 10/2003 | Gillespie et al. |
| D481,872 S | 11/2003 | Hennel et al. |
| 6,647,549 B2 | 11/2003 | McDevitt et al. |
| 6,669,878 B2 | 12/2003 | Yamada et al. |
| 6,716,498 B2 | 4/2004 | Curro et al. |
| 6,726,870 B1 | 4/2004 | Benson et al. |
| 6,736,916 B2 | 5/2004 | Steinke et al. |
| 6,739,024 B1 | 5/2004 | Wagner |
| 6,794,626 B2 | 9/2004 | Kiermeier et al. |
| 6,808,791 B2 | 10/2004 | Curro et al. |
| 6,818,802 B2 | 11/2004 | Takai et al. |
| 6,830,800 B2 | 12/2004 | Curro et al. |
| 6,837,956 B2 | 1/2005 | Cowell et al. |

(56) References Cited

U.S. PATENT DOCUMENTS

| | | |
|---|---|---|
| 6,846,172 B2 | 1/2005 | Vaughn et al. |
| 6,855,220 B2 | 2/2005 | Wildeman et al. |
| 6,863,960 B2 | 3/2005 | Curro et al. |
| 6,872,274 B2 | 3/2005 | Kauschke et al. |
| 6,884,494 B1 | 4/2005 | Curro et al. |
| 7,005,558 B1 | 2/2006 | Johansson et al. |
| 7,037,569 B2 | 5/2006 | Curro et al. |
| 7,297,226 B2 | 11/2007 | Schulz |
| 7,402,723 B2 | 7/2008 | Stone et al. |
| 7,521,588 B2 | 4/2009 | Stone et al. |
| 7,655,176 B2 | 2/2010 | Stone et al. |
| 2002/0039867 A1 | 4/2002 | Curro et al. |
| 2002/0103469 A1 | 8/2002 | Chen et al. |
| 2002/0105110 A1 | 8/2002 | Dobrin et al. |
| 2002/0107495 A1 | 8/2002 | Chen et al. |
| 2002/0119720 A1 | 8/2002 | Arora et al. |
| 2002/0132544 A1 | 9/2002 | Takagaki et al. |
| 2003/0021951 A1 | 1/2003 | Desai et al. |
| 2003/0028165 A1 | 2/2003 | Curro et al. |
| 2003/0085213 A1 | 5/2003 | Burckhardt et al. |
| 2003/0191442 A1 | 10/2003 | Bewick-Sonntag et al. |
| 2003/0191443 A1 | 10/2003 | Taylor et al. |
| 2003/0201582 A1 | 10/2003 | Gray |
| 2004/0126531 A1 | 1/2004 | Gerner et al. |
| 2004/0121686 A1 | 6/2004 | Wong et al. |
| 2004/0122396 A1 | 6/2004 | Maldonado et al. |
| 2004/0131820 A1 | 7/2004 | Turner et al. |
| 2004/0137200 A1 | 7/2004 | Chhabra et al. |
| 2004/0157036 A1 | 8/2004 | Provost et al. |
| 2004/0209041 A1 | 10/2004 | Muth et al. |
| 2004/0229008 A1 | 11/2004 | Hoying et al. |
| 2004/0242097 A1 | 12/2004 | Hasenoehrl et al. |
| 2004/0265533 A1 | 12/2004 | Hoying et al. |
| 2004/0265534 A1 | 12/2004 | Curro et al. |
| 2005/0064136 A1 | 3/2005 | Turner et al. |
| 2005/0096614 A1 | 5/2005 | Perez et al. |
| 2005/0123726 A1 | 6/2005 | Broering et al. |
| 2006/0019056 A1 | 1/2006 | Turner et al. |
| 2006/0087053 A1 | 4/2006 | O'Donnell et al. |
| 2007/0029694 A1 | 2/2007 | Cree et al. |
| 2008/0224351 A1 | 9/2008 | Curro et al. |
| 2009/0026651 A1 | 1/2009 | Lee et al. |
| 2010/0233428 A1 | 3/2010 | Stone |
| 2010/0102488 A1 | 4/2010 | Stone et al. |
| 2010/0230857 A1 | 9/2010 | Muhs et al. |
| 2010/0230858 A1 | 9/2010 | Stone et al. |
| 2010/0230866 A1 | 9/2010 | Gray et al. |
| 2010/0230867 A1 | 9/2010 | Gray et al. |
| 2010/0233438 A1 | 9/2010 | Stone et al. |
| 2010/0233439 A1 | 9/2010 | Stone et al. |
| 2010/0247844 A1 | 9/2010 | Curro et al. |
| 2010/0255258 A1 | 10/2010 | Curro et al. |
| 2012/0064280 A1 | 3/2012 | Hammons et al. |
| 2012/0064298 A1 | 3/2012 | Orr et al. |
| 2012/0273146 A1 | 11/2012 | Curro et al. |
| 2012/0273148 A1 | 11/2012 | Orr et al. |
| 2012/0273990 A1 | 11/2012 | O'Donnell et al. |
| 2012/0276238 A1 | 11/2012 | Strube et al. |
| 2012/0276341 A1 | 11/2012 | Lake et al. |
| 2012/0276637 A1 | 11/2012 | Zhou et al. |
| 2012/0277393 A1 | 11/2012 | Curro et al. |
| 2012/0277704 A1 | 11/2012 | Marinelli et al. |
| 2012/0277705 A1 | 11/2012 | Marinelli et al. |
| 2012/0277706 A1 | 11/2012 | Marinelli et al. |
| 2012/0277707 A1 | 11/2012 | Orr et al. |
| 2012/0277708 A1 | 11/2012 | Marinelli et al. |
| 2012/0277709 A1 | 11/2012 | Marinelli et al. |
| 2012/0277710 A1 | 11/2012 | Marinelli et al. |
| 2012/0295060 A1 | 11/2012 | Mullane et al. |

FOREIGN PATENT DOCUMENTS

| | | |
|---|---|---|
| EP | 0963747 | 12/1999 |
| EP | 0598970 | 4/2000 |
| EP | 1004412 | 5/2000 |
| GB | 900083 | 9/2009 |
| WO | WO9515138 | 6/1995 |
| WO | WO02100632 | 12/2002 |
| WO | WO05011936 A1 | 2/2005 |
| WO | WO2005011936 | 2/2005 |

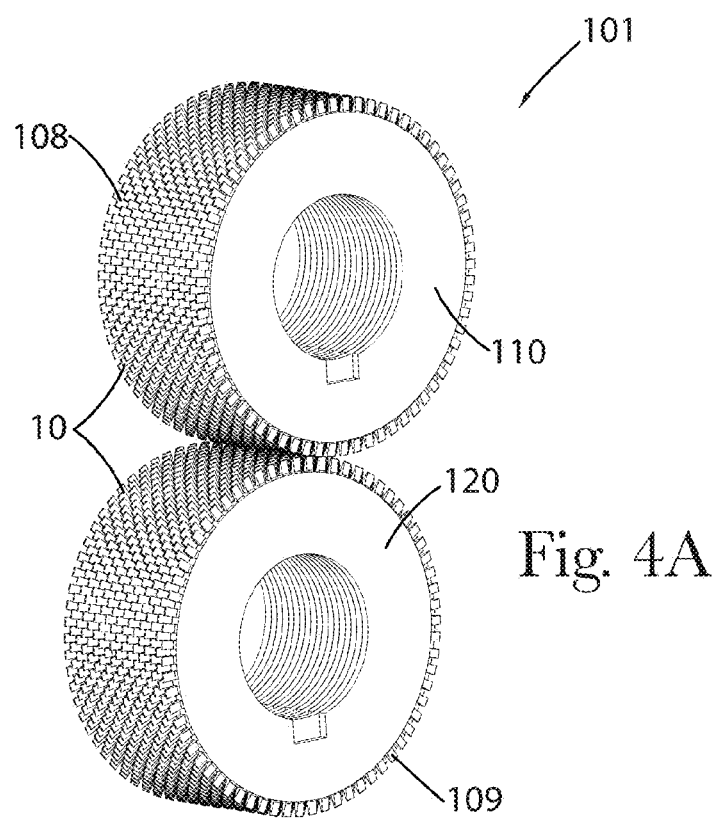
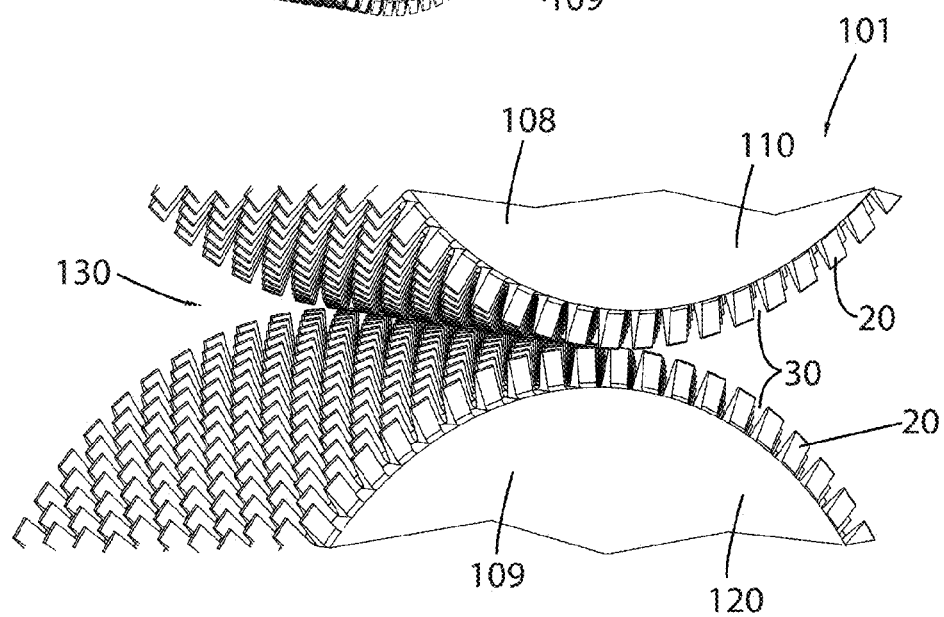
Fig. 4A
Fig. 4B

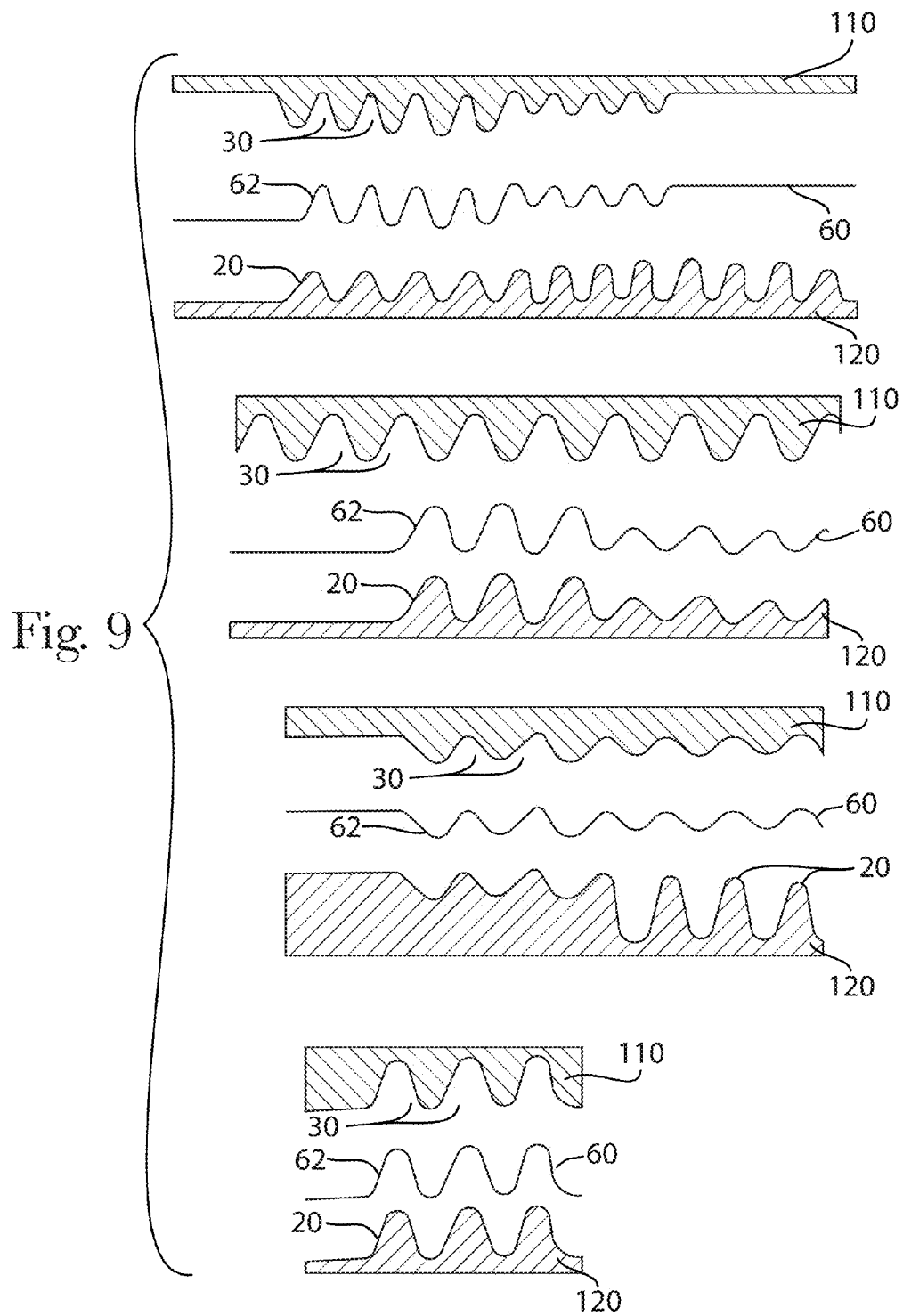

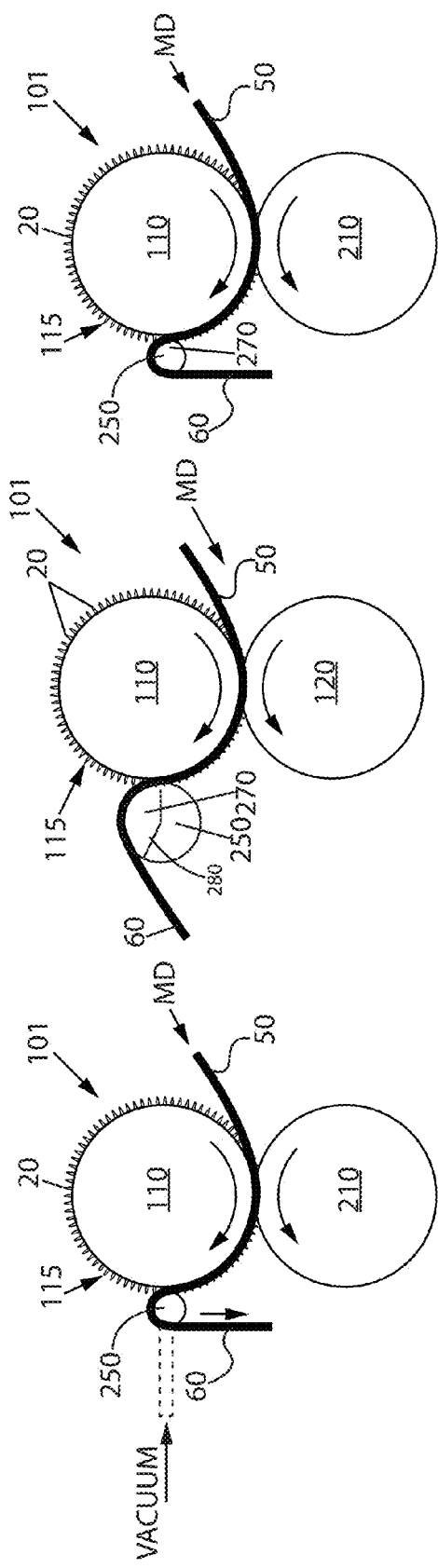

second direction (MD view)

second direction (MD view)

first direction (MD view)

PROCESS FOR MAKING A MICRO-TEXTURED WEB

FIELD OF THE INVENTION

The present invention is directed to a process for deforming a precursor web to create a micro-textured web. Specifically, the process can be used to make three-dimensional micro-textured films, nonwovens, and laminates thereof.

BACKGROUND OF THE INVENTION

Webs, such as thermoplastic films, have a variety of uses including component materials of absorbent articles (such as topsheets and backsheets), packaging (such as flow wrap, shrink wrap, and polybags), trash bags, food wrap, dental floss, wipes, electronic components, and the like. For many of these uses of webs, it can be beneficial for the web to have a textured, three-dimensional surface which can provide the surface of the web with a desirable feel (e.g., soft, silky), visual impression, and/or audible impression, as well as one or more desirable properties, such as improved fluid handling or strength.

Webs exhibiting a desirable feel can be made via a vacuum forming process, wherein a precursor web is heated and placed over a forming structure. Then a vacuum forces the precursor web to conform to the texture of the forming structure. Vacuum forming processes are typically limited with respect to the amount of pressure capable of being exerted onto a precursor web and hence are inefficient due to the necessary heating step and the limited pressures generated.

Webs exhibiting a desirable feel can also be made via a hydroforming process, wherein a precursor web is placed over a forming structure and high pressure and high temperature water jets force the precursor web to conform to the texture of the forming structure. A hydroforming process, although capable of producing soft and silky polymeric webs, is typically a costly and inefficient process involving the use of high pressure and high temperature water jets and subsequent drying steps, including dewatering steps.

Webs exhibiting a desirable feel can also be made via an embossing process, wherein a substrate is mechanically worked to cause the substrate to conform under pressure to the depths and contours of a pattern engraved or otherwise formed on an embossing roll. Embossing processes typically require heating and cooling steps which add undesirable cost and inefficiency, as well as complexity, to the process. In addition, such embossing processes typically involve relatively large dwell times, which can result in slow, inefficient processes. Or, processes are known wherein a substrate is placed between a forming structure and a compliant material, such as rubber, to enable embossing at relatively low temperatures, as described in US 2010/0230857 and US 2010/0230858. Such processes require high pressure and deformations resulting in equipment wear and reduced lifetime.

While various processes to make textured webs are known, these processes have numerous drawbacks, such as cost, complexity, speed of manufacturing, difficulty creating small tooling, durability of tooling, predictable results, etc. Solid state processes using tooling with two mated, rigid structures have the benefits of low cost, high speed, and durable tooling. However, these processes have been limited to relatively large distances between forming elements as well as relatively large structures; it is difficult to impart relatively small scale texture to precursor webs using conventional forming structures. Further, the ability to make, with solid state formation techniques (generally, any process which occurs at a temperature below the melt point of the polymer or material being processed), a micro-textured web comprising three-dimensional features having either open- or closed-distal ends and location-controlled thinning has not been described.

Accordingly, there remains a need to make micro-textured webs, including formed film webs, using low cost, high speed processes. There is a desire for processes and apparatuses that are capable of forming new structures in webs that provide the webs with a micro-texture, and thus, a desirable feel, visual impression, and/or audible impression as well as additional properties. In the case of webs used in absorbent articles, such new processes and apparatuses may include those that provide a single portion of the web with dual, or more, properties (such as improved softness, fluid handling, or other properties) in a predetermined location on the web. A need also exists for processes and apparatuses that will allow a web to be deformed multiple times while maintaining control over the registration of the deformations in the web. One objective of the present invention is to impart sufficient web tension and/or friction between a web and a pair of forming structures to allow a micro-textured web to form.

SUMMARY OF THE INVENTION

Disclosed herein are processes for making micro-textured webs. One specific process comprises the steps of: (a) providing a precursor web; (b) providing a first pair of mated forming members including a first forming member and a second forming member forming a first deformation zone therebetween, wherein the first forming member comprises a plurality of protrusions and wherein at least the second forming member comprises a plurality of voids; (c) moving the precursor web through the first deformation zone, wherein the voids of the second forming member engage with the protrusions of the first forming member at an engagement position thereby forming a first plurality of structures on the precursor web; (d) providing a second pair of mated forming members including a third forming member and a fourth forming member forming a second deformation zone therebetween, wherein the third forming member comprises a plurality of voids and the fourth forming member comprises a plurality of protrusions; (e) moving the precursor web through the second deformation zone, wherein the voids of the third forming member engage with the protrusions of the fourth forming member at an engagement position thereby forming a second plurality of structures on the precursor web, wherein the first plurality of structures is different than the second plurality of structures.

Another process pertains to a method of creating a disposable absorbent article. This process comprises the steps of: (a) providing a precursor web; (b) providing a first pair of mated forming members including a first forming member and a second forming member forming a first deformation zone therebetween, wherein the first forming member comprises a plurality of protrusions and wherein at least the second forming member comprises a plurality of voids; (c) moving the precursor web through the first deformation zone, wherein the voids of the second forming member engage with the protrusions of the first forming member at an engagement position thereby forming a first plurality of structures on the precursor web; (d) providing a second pair of mated forming members including a third forming member and a fourth forming member forming a second deformation zone therebetween, wherein the third forming member comprises a plurality of voids and the fourth forming member comprises a plurality of protrusions; (e) moving the precursor web through the second deformation zone, wherein the voids of the third forming member engage with the protrusions of the fourth forming member at an engagement position thereby forming a second plurality of structures on the precursor web, wherein the first plurality of structures is different than the second plurality of structures; and (f) utilizing the precursor web as a topsheet for an absorbent article.

Another process for making a micro-textured web comprises the steps of providing a precursor web; providing a pair of mated forming members including a first forming member and a second forming member forming a first deformation zone therebetween, wherein the first forming member comprises a first plurality of forming elements in a first portion, a second plurality of forming elements in a second portion, and a first plurality of voids in a third portion disposed between the first portion and the second portion, and wherein the second forming member comprises a first plurality of voids in a first portion, a second plurality of voids in a second portion, and a first plurality of forming elements in a third portion disposed between the first portion and second portion; and moving the precursor web through the first deformation zone, wherein the first plurality of forming elements of the first forming member engage the first plurality of voids of the second forming member, the second plurality of forming elements of the first forming member engage the second plurality of voids of the second forming member, and wherein the first plurality of forming elements of the second forming member engage the first plurality of voids in the first forming member, thereby forming a first plurality of structures on the precursor web and a second plurality of structures on the precursor web, wherein the first plurality of structures and the second plurality of structures extend in different directions from the precursor web.

BRIEF DESCRIPTION OF THE DRAWINGS

The following detailed description of specific embodiments of the present invention can be best understood when read in conjunction with the drawings enclosed herewith.

FIGS. 4A and 4B are perspective views of another pair of mated forming structures;

FIG. 9 is a representation of forming structures and a web with varying amplitudes;

FIGS. 21A-E illustrate exemplary web release mechanisms;

DETAILED DESCRIPTION

Figure 1:
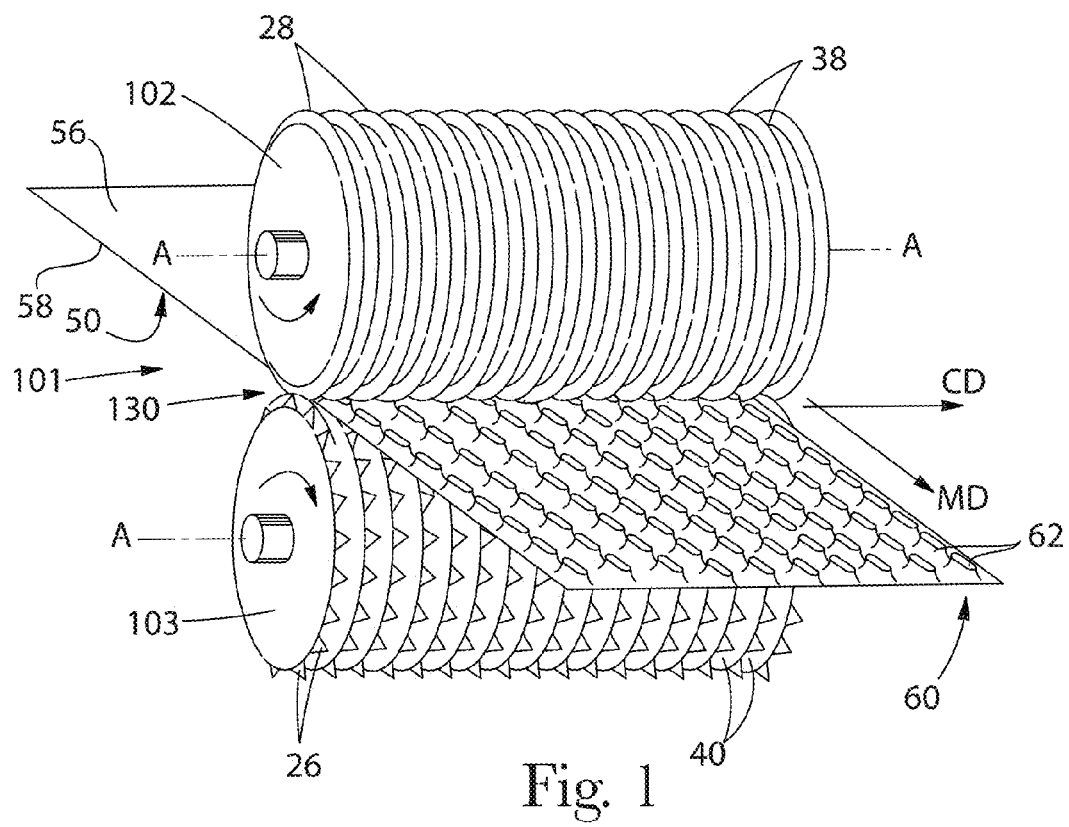
FIG. 1 is a perspective view of a pair of mated forming structures.

The present invention is directed to a process for forming a micro-textured web that overcomes one or more of the aforementioned shortcomings of the prior art. For example, embodiments of the new process impart a very small-scale texture to webs. Compared to prior art solid state formation processes, embodiments of the new process allow for the formation of a web which comprises more tightly-spaced discrete three-dimensional elements ("3-D elements") having open proximal ends and open or closed distal ends or sidewalls. Furthermore, embodiments of the new process enable the creation of webs having 3-D elements comprising features such as sidewall thinning or non-fully connected elements. For example, non-fully connected elements may include flaps, which are only partially attached around their periphery and therefore provide additional softness due to their rotational degrees of motion. In the case of webs used in absorbent articles, such new structures may include those that provide a single portion of the web with multiple properties (such as improved softness, fluid handling, or other properties) in a predetermined portion of the web. The processes can allow a web to be deformed multiple times while maintaining control over the registration of the deformations in the web.

The process generally includes a forming step in which a precursor web is moved through a micro-texturing deformation zone located between a pair of mated forming structures. The forming structures each comprise forming elements such as protrusions and voids. The resultant web includes a plurality of closely-spaced, discrete 3-D elements, thereby providing a micro-textured web. The process may also include an additional forming step in which the micro-textured web is moved through at least one other micro- or macro-texturing deformation zone located between a second pair of mated forming structures. The additional deformation process may be before or after the micro-texturing step described herein. The resultant web includes a plurality of closely-spaced, discrete 3-D elements imparted by the first forming step, as well as micro or macro features imparted by the second forming step, thereby providing a complex micro-textured web. The second discrete 3-D elements may extend from the first or second side of the web. For example, a topsheet for an absorbent hygiene article may be formed which has a micro-texture as well as a macro-texture. Alternatively, the second forming step can include the same geometry forming elements so as to place elements between those of the first forming step, thereby increasing the area density of the micro-texture.

Advantageously, the process disclosed herein can allow for use of rigid forming structures having narrower center-to-center spacing between adjacent forming elements as well as a higher area density of forming elements to produce micro-textured webs having smaller scale spacing between adjacent discrete 3-D elements and a high density of discrete 3-D elements. Previously, rigid forming structures were designed to have fewer forming elements and wider spacing between adjacent elements because they were cheaper and easier to manufacture and had significantly increased life span as compared to forming structures having a higher area density of forming elements with narrower spacing between adjacent elements. Processes exist for making a micro-textured web using a compliant material, such as water, rubber, and air in conjunction with a rigid structure; however, up to this point, two rigid mated forming structures have not been able to create micro-textured webs with such small scale. It has been discovered that applying the forming structure techniques such as those disclosed in U.S. Pat. No. 7,655,176 to create both of the rigid, mated forming structures of the present invention can allow high speed innovative tooling for processes of the current invention. Now, it is possible to create small length scales of protrusions and voids on pairs of rigid mated forming structures.

Forming Structures

Figure 2:
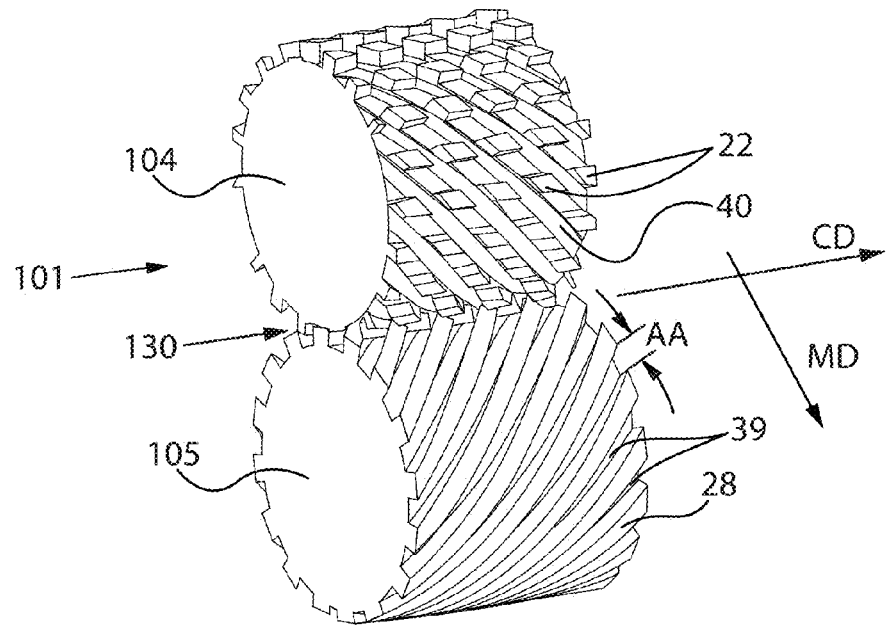
FIG. 2 is a perspective view of another pair of mated forming structures.
Figure 3:
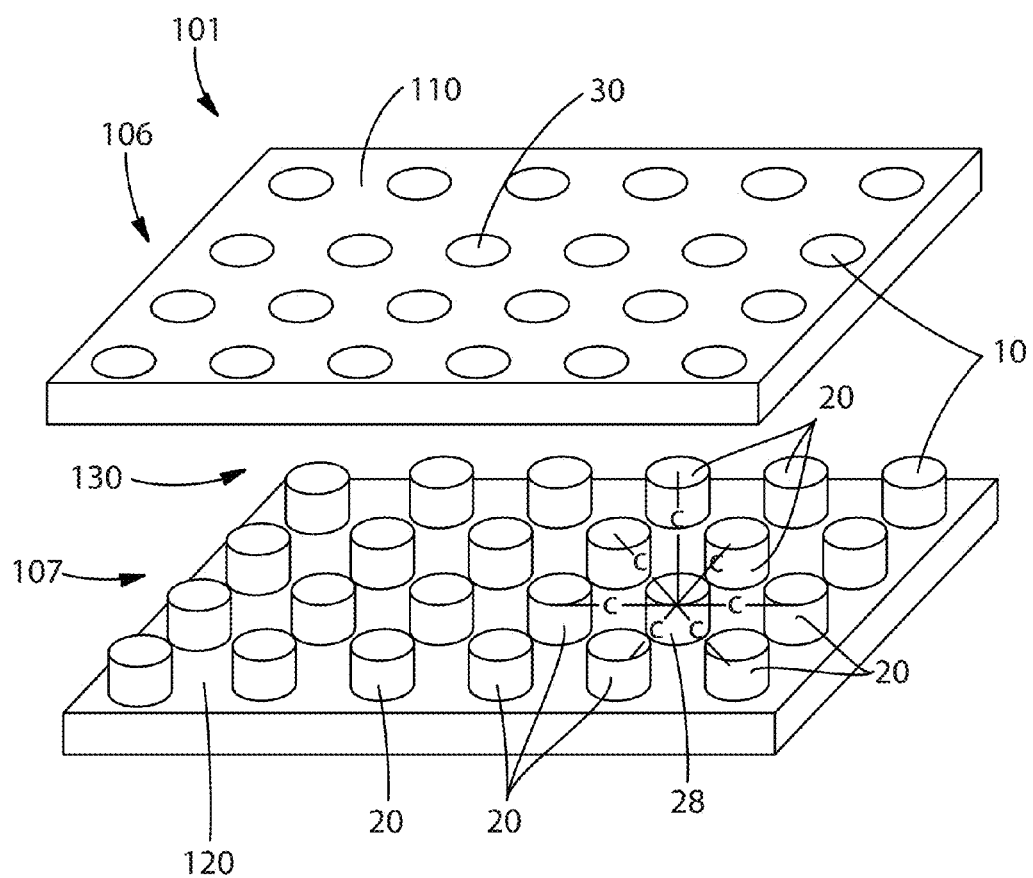
FIG. 3 is a perspective view of another pair of mated forming structures.

The micro-texturing process can be carried out via an apparatus that comprises a pair of rigid mated forming structures, such as those shown in FIGS. 1-3. Forming structures may comprise rollers, plates, belts, sleeves, or the like, or combinations thereof. Suitable pairs of forming structures 101 include, but are not limited to: a pair of counter-rotating rollers that define a nip therebetween, a pair of plates, and a pair of belts. In one embodiment, as shown in FIG. 1, the pair of mated forming structures 101 is a pair of counter-rotating rollers 102,103 which engage in the machine direction MD. Using a forming apparatus with rollers can be beneficial in the case of continuous processes, particularly those in which the speed of the process is of interest. In another embodiment, as shown in FIG. 2, the pair of mated forming structures 101 is a pair of counter-rotating rollers 104,105 which engage at an angle AA from the machine direction MD. In another embodiment, as shown in FIG. 3, the pair of mated forming structures 101 is a pair of plates 106,107. In another preferred embodiment, the pair of mated forming structures may comprise an endless belt. Referring to FIGS. 3, 4A, and 4B, individual forming structures 110,120 (or any additional forming structures 210,220 of additional texturing steps) for use in the process of the present disclosure include a plurality of forming elements 10. As used herein, "forming structures" refer generally to structures capable of imparting a texture to a web. As used herein, "forming elements" refer generally to elements that provide texture to a web; types of forming elements include discrete protrusions, discrete voids, continuous voids, or combinations thereof. Forming elements may vary in shape, size, sharpness, taper, aspect ratio, and/or center-to-center spacing. One type or multiple types of forming elements 10 can be present on a single forming structure. Generally, a pair of mated forming structures comprises at least two types of forming elements. For example, the first forming structure 110 may include voids 30 while the second forming structure 120 may include protrusions 20. Alternatively, the first and second forming structures 110,120 may have the same type of forming elements 10; for example, both forming structures 110,120 can include protrusions 20 and voids 30, as illustrated in FIGS. 4A and 4B. In the embodiment shown in FIG. 4B, the spaces between adjacent protrusions 20 act as voids 30. The term "adjacent," as used herein, with reference to features or regions, means near or close to, and which need not be in contact with each other.

Figure 5:
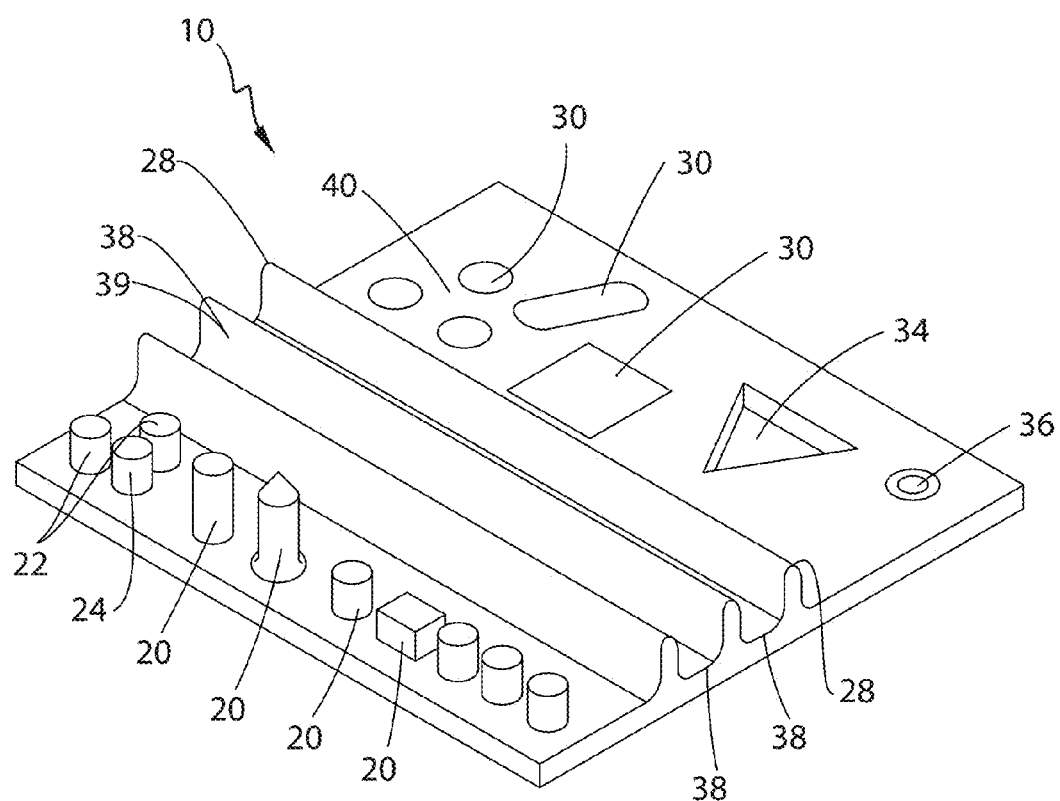
FIG. 5 is a perspective view of a portion of a forming structure.

As illustrated in FIG. 5 the forming elements 10 of either or both of the first and second forming structures 110,120 can include protrusions 20 or voids 30 selected from discrete protrusions 22 (e.g., pillars 24 or teeth 26), ridges 28, discrete voids 32 (e.g., apertures 34 or depressions 36), continuous voids 38, grooves 39, or a combination thereof. The forming structures 110,120 can further include lands 40 completely surrounding the forming elements 10. The forming elements 10 of the forming structures 110,120 can be small in scale relative to typical patterns used on forming structures 110,120 in conventional texturing or embossing processes. The process of the disclosure can produce micro-textured webs 60 (See e.g., FIGS. 11-14) that include relatively high aspect ratio 3-D elements 62 with thinned distal ends 66 and/or sidewalls 70, even without heating webs and even at high speeds.

Figure 6:
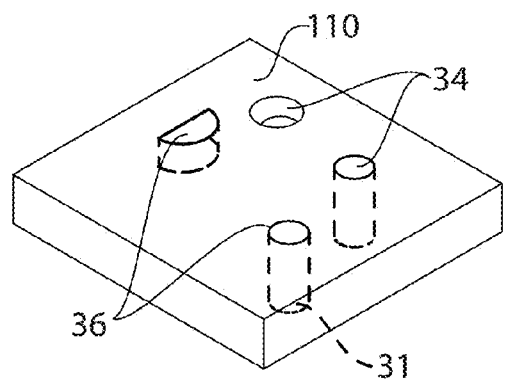
FIG. 6 is a perspective view illustrating apertures and depressions.

FIG. 6 illustrates the distinction between two exemplary types of discrete voids 32 described herein: apertures 34 and depressions 36. As used herein, "apertures 34" refers to an opening in the forming structures 110,120 that does not include a bottom surface limiting the depth of the opening. In contrast, as used herein, "depressions 36" refers to an opening in the forming structures 110,120 having a bottom surface, or valley 31, limiting the depth of the opening to be less than the thickness of the forming structures 110,120. The valley 31 can be, for example, porous or non-porous. The valley 31 can include an opening having a width smaller than the diameter of the depression 36, which vents the depression 36 by allowing air to pass through the depression 36. For example, the valley 31 opening may have a width smaller than the thickness of the precursor web 50. The valley 31 can be flat, rounded, or sharp.

As used herein, "grooves 39" are voids 30 which are non-circular in cross-section, have a length greater than a width, and are sized to encompass one or more protrusions 20. The length of the grooves 39 may be aligned with a machine direction MD or cross direction CD, or skewed a certain degree from the machine direction or cross direction or combinations thereof. Referring back to FIG. 2, the pair of skewed rollers 104 comprises grooves 39. In certain embodiments, the grooves are skewed, meaning they run at an angle AA of 5° to 85°, 15° to 75°, 25° to 65°, or 45° from the machine direction. Engaging forming rollers at an angle skewed to the machine direction MD can result in structures which have greater strength and/or softness (as well as a different visual appearance than if it were machine direction-aligned only) depending upon the use of the micro-textured web 60.

The forming structures 110,120 can be a solid roll, or have a thickness of 25 to 25,000 microns, or 100 to 5,000 microns. The voids 30 can have a depth of 10 to 500 microns, or 25 to 5000 microns. As used herein, the depth of the aperture 34 corresponds to the thickness of the forming structures 110,120 because the aperture 34 has no bottom surface limiting its depth. In one embodiment the voids 30 can have a depth substantially equal to the thickness of at least one of the webs, at least twice the thickness of at least one of the webs, or at least three times the thickness of at least one of the webs. Preferably, the voids 30 have a depth that is at least three times the total thickness of the webs.

The perimeter of the voids 30 on the web contacting surface of the forming structures 110,120 can have a straight edge or can have a radius of curvature as measured from the web contacting surface of the forming structures 110,120 into the void 30. The radius of curvature can be 0 to 2000 microns, preferably 0 to 25 microns, and more preferably 2 to 25 microns. In one embodiment, an angled taper, commonly known as a chamfer, is used. In one embodiment a combination of straight edges and radii are used.

The voids 30 have at least one diameter, which for a generally cylindrical structure is the inside diameter. For example, a discrete void 32 may take the shape of an oval, while a continuous void 38 may take the shape of a groove 39; each void having two diameters, one in the length direction and one in the width direction. The diameter of the void 30 may be sized to encompass one or more protrusions. FIGS. 7A-D illustrate exemplary combinations of voids 30 and protrusions 20. At an engagement position 140 of the forming structures 110,120, there is a sidewall clearance 42 and a tip-to-valley clearance 44 between protrusions 20 and voids 30. The diameter of the void depends upon the diameter (or width for non-uniform and/or non-cylindrical voids) of the one or more protrusions, plus the sidewall clearance. Each void 30 can have diameter of 40 to 2,000 microns, 50 to 500 microns, 65 to 300 microns, 75 to 200 microns, or 10 to 5000 microns, 50 to 5000 microns, 500 to 5000 microns, or 800 to 2,500 microns.

The diameter of a void 30 may be constant, decreasing with increasing depth, or increasing with increasing depth. For example, the voids 30 can have a first diameter at a first depth and a second diameter at a second depth deeper than the first depth. For example, the first diameter can be larger than the second diameter, i.e., inward taper. Or, for example, the second diameter can be larger than the first diameter, i.e., outward taper. The sidewalls of the voids 30 can be completely vertical, tapered, curved, or the sidewalls can include combinations thereof. In one embodiment, the voids 30 have tapered sidewalls. In one embodiment, sidewalls with an inward taper will typically have a degree of taper of 0° to 50°, 2° to 30°, or 5° to 25°. In another embodiment, the sidewalls of the voids comprise a combination of vertical and curved sidewalls.

Figure 7A:
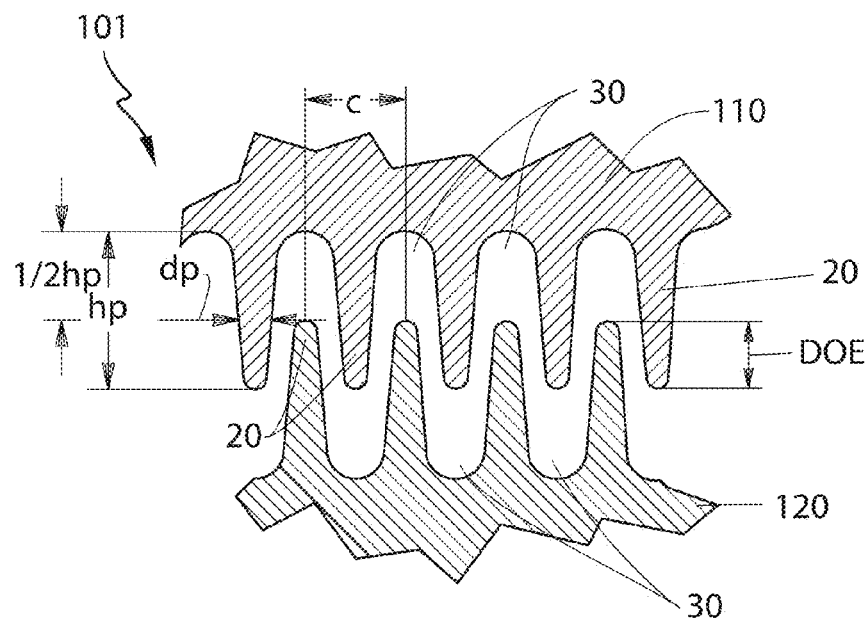
FIGS. 7A-D illustrate exemplary combinations of voids 30 and protrusions 20.
Figure 7B:
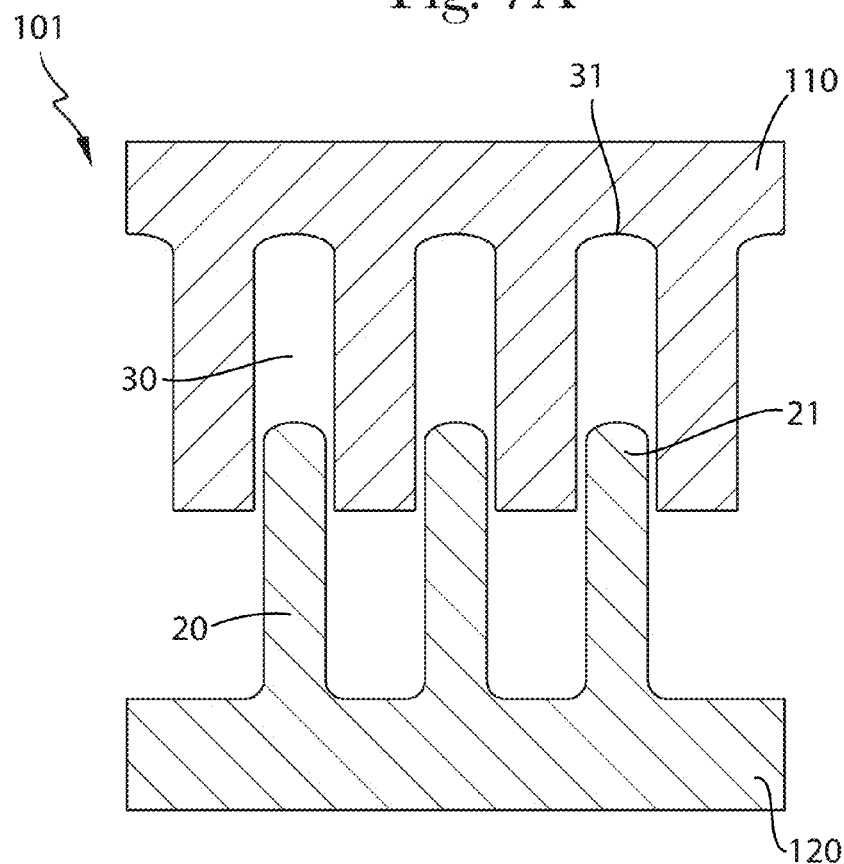
Figure 7C:
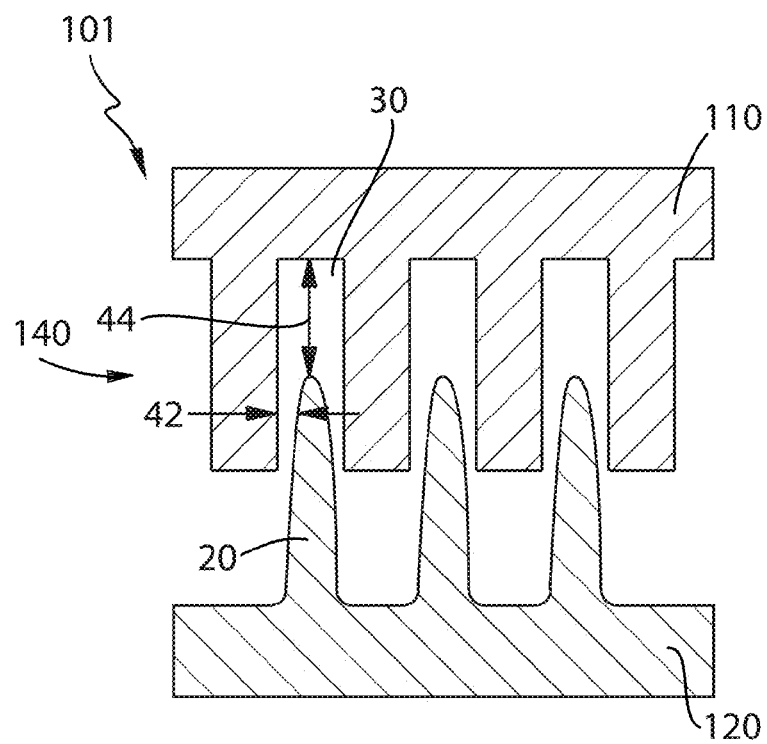
Figure 7D:
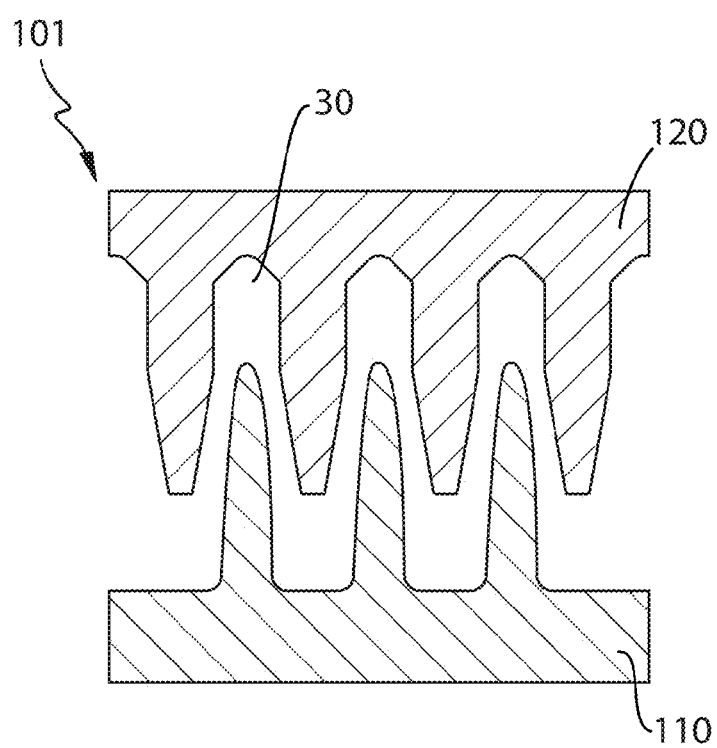
Figure 8A:
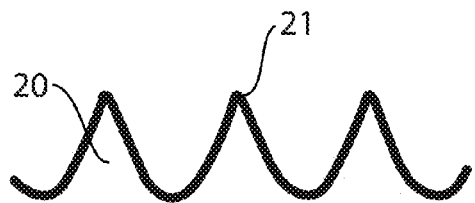
FIGS. 8A-H are illustrations of various protrusion geometries.
Figure 8B:
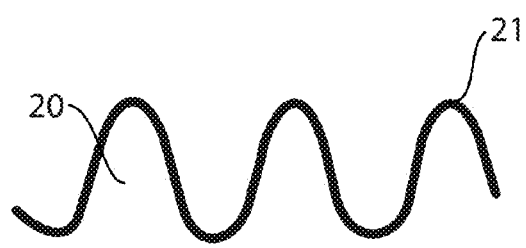
Figure 8C:
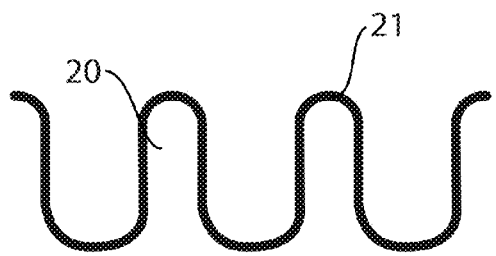
Figure 8D:
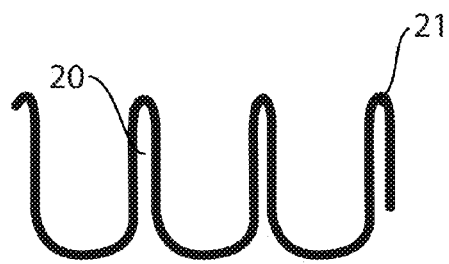
Figure 8E:
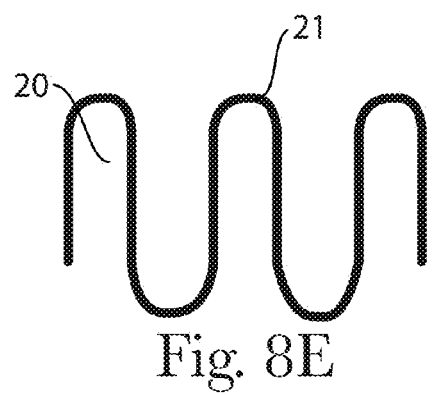
Figure 8F:
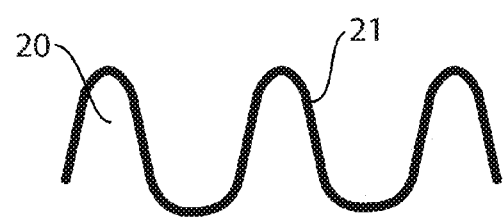
Figure 8G:
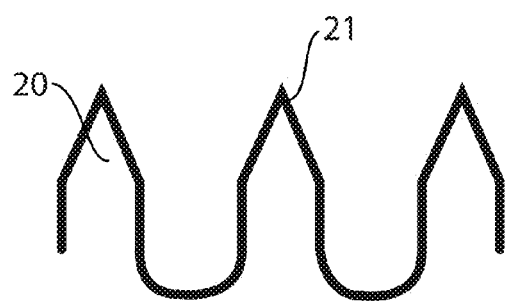
Figure 8H:
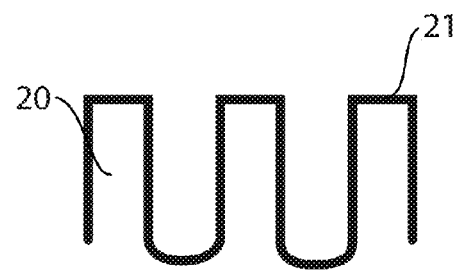

Protrusions 20 on one forming structure 110,120 can have varying heights or the substantially same height. The protrusions 20 can have heights of 100 microns to 2,000 microns, at least 500 microns, at least 700 microns, at least 900 microns, or at least 1,100 microns. In one embodiment the protrusions 20 can have a height substantially equal to the thickness of at least one of the webs, at least twice the thickness of at least one of the webs, or at least three times the thickness of at least one of the webs. Preferably, the protrusions 20 have a height that is at least three times the total thickness of the webs. The protrusions 20 can have a diameter, which for a generally cylindrical structure is the outside diameter. For non-uniform cross-sections, and/or non-cylindrical structures of protrusions 20, diameter dp is measured as the average cross-sectional dimension of protrusions 20 at ½ the height hp of the protrusions 20, as shown in FIG. 7A. The protrusions 20 can have diameter dp that can be from 10 microns to 770 microns, 50 microns to 600 microns, 50 microns to 500 microns, 65 microns to 400 microns, or 75 microns to 300 microns. In one embodiment, the protrusions 20 of the forming structures 110,120 will have a diameter of less than 700 microns.

Various protrusion shapes are shown in FIGS. 8A-H. The protrusions 20 of the forming structures 110,120 can have distal ends, or tips 21 that are flat, rounded or sharp, depending upon whether it is desired to produce a micro-textured web 60 having three-dimensional elements ("3-D elements") 62 with distal ends 66 that are open, or apertured 67 (requiring a sharper protrusion on the forming structure 110) or closed 68 (requiring a more rounded protrusion on the forming structure 110). Less sharp or rounded protrusion tips 21 may lead to more side thinning of the sidewalls 70 of the 3-D elements 62 and even rupturing to form side openings, or apertures 71. In some embodiments, the tips 21 of the protrusions 20 of the forming structures 110,120 are rounded and have a certain tip radius, such as from 5 to 300 microns, from 10 to 150 microns, from 15 to 100 microns, from 20 to 75 microns, or from 30 to 60 microns.

The sidewalls of the protrusions 20 can be completely vertical, tapered, curved, or combinations thereof. Tapered sidewalls can also allow the web 60 to more easily separate from the forming structures 110,120 after micro-texturing. In one embodiment, the sidewalls will typically have a degree of taper of from 0° to 50°, from 2° to 30°, or from 5° to 25°. In other embodiments, the protrusions 20 can be spherical, ellipsoid, or snowman-shaped, having different or varying diameters along the height of the protrusion 20. In a preferred embodiment, protrusions 20 comprise tips 21 with a smaller radii and sidewalls with a steeper degree of taper.

Forming elements 10 of a single forming structure 110, 120 can have varying geometries, such as height of the protrusions 20 and depth of the voids 30, or combinations of both. For example, the forming elements 10 can gradually increase in height or over a range of tens or hundreds of adjacent protrusions 20, which can result in the web 60 having discrete 3-D elements 62 with varying heights. Other features of the forming structures 110,120 which result in corresponding features of the discrete 3-D elements 62 can be adjusted to form gradient characteristics in the discrete 3-D elements 62 of the micro-textured web 60. As shown in FIG. 9, the forming structures 110,120 can include an area density gradient of forming elements 10.

Figure 10A:
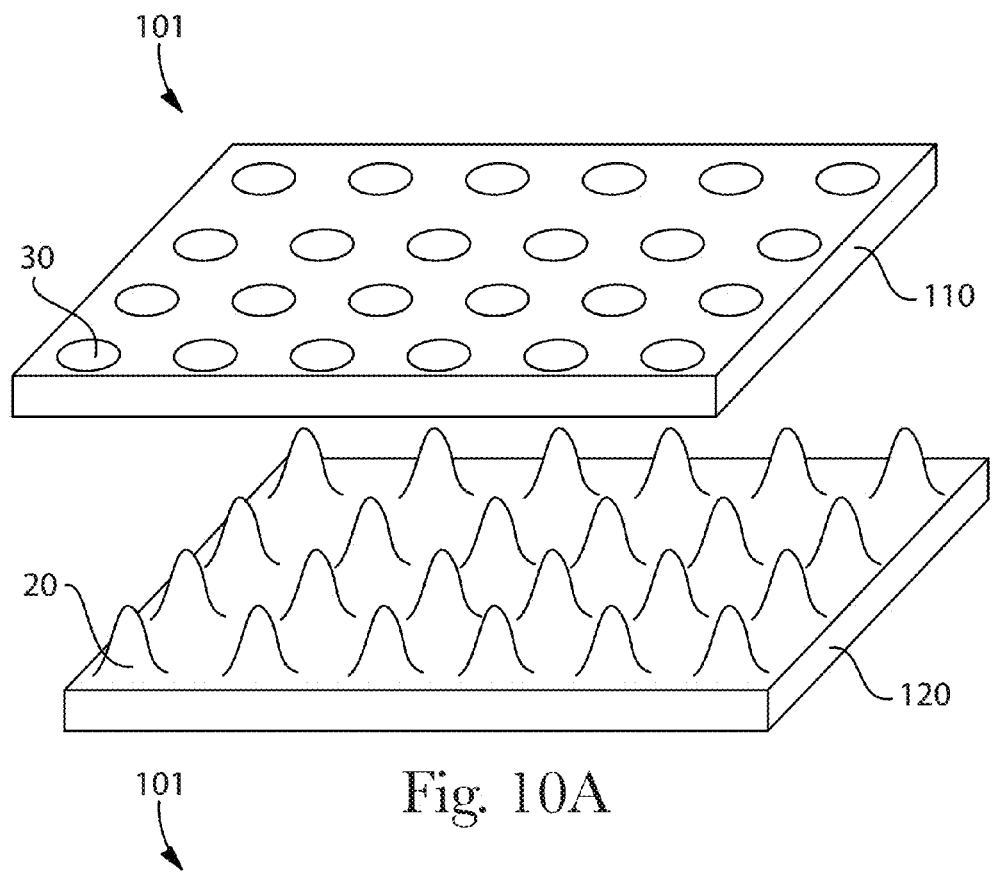
FIGS. 10A-C are illustrations of different ratios of protrusions to voids.
Figure 10B:
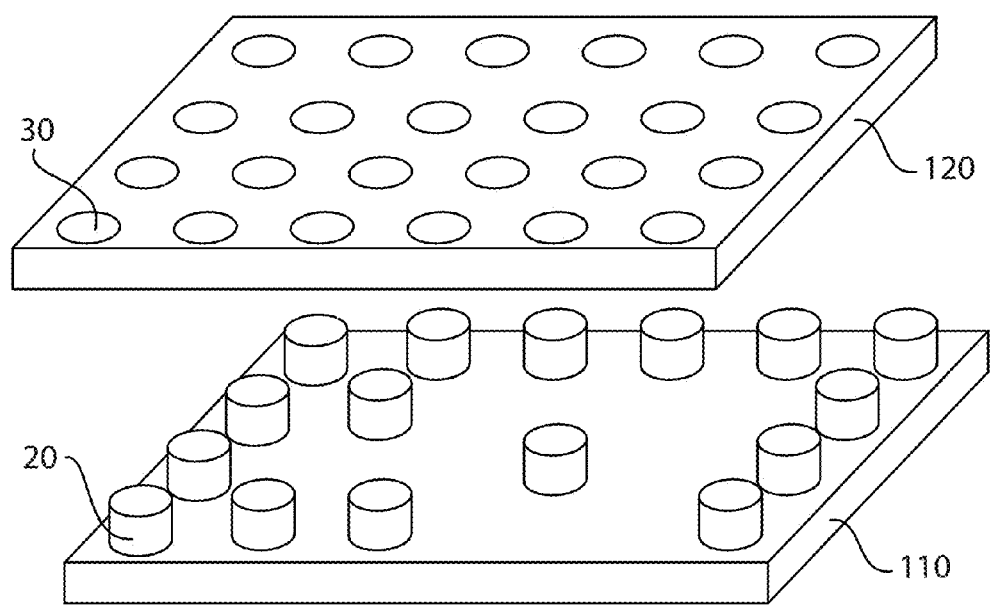
Figure 10C:
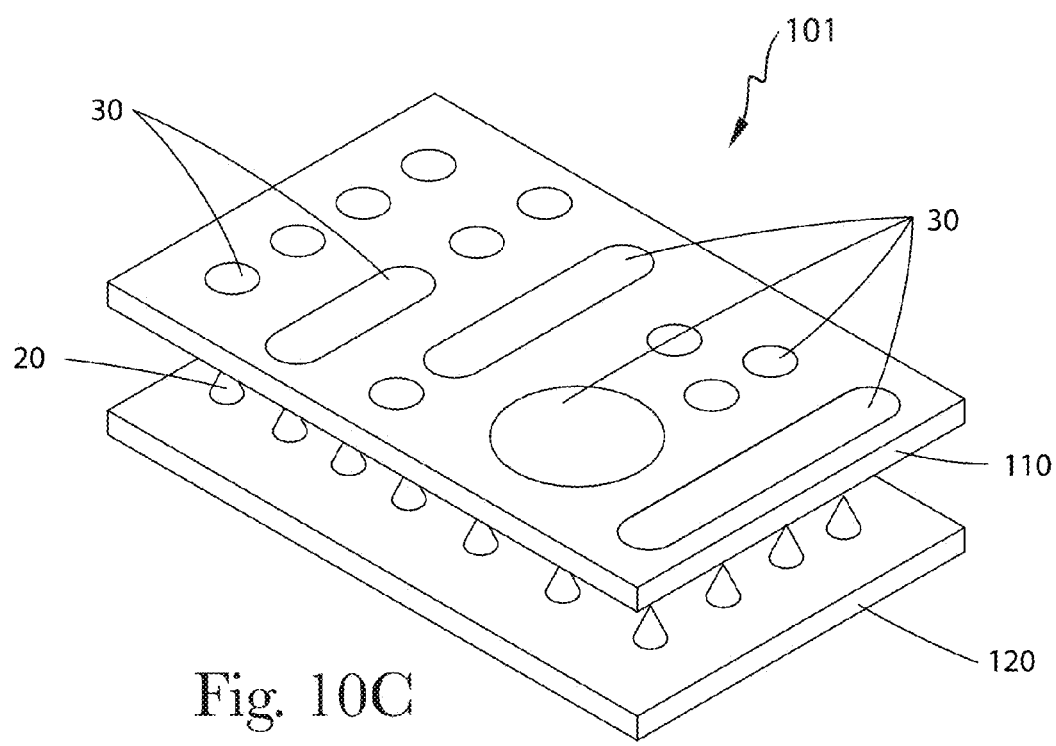

FIGS. 10A-C show various ratios of protrusions 20 to voids 30 on forming structures 110,120. In some embodiments, the protrusions 20 and voids 30 are sized relative to one another to allow mating to successfully produce a micro-textured web 60 of the present invention. The ratio of protrusions 20 to voids 30 may be 1:1 so that each protrusion 20 has a corresponding void 30, such as shown in FIG. 10A. Or, the ratio of protrusions 20 to voids 30 may be less than 1:1, so that there are extra voids 30 which do not match up to protrusions 20, as shown in FIG. 10B. Extra voids 30 may simplify alignment of two mated forming structures. Or, the ratio of protrusions 20 to voids 30 may be greater than 1:1, for instance, two, three, four, or more protrusions 20 may be sized to mate with only one void 30, as shown in FIG. 10C. The ratio of protrusions 20 to voids 30 may range from at least about 1:1, at least about 100:1, at least about 10,000:1, or even more, such as when multiple discrete protrusions 22 mate with one continuous void 38, as shown in FIG. 1. In other embodiments, the protrusions 20 need not mate with voids 30, but can mate with the void 30 spaces between other protrusions 20. For example, FIGS. 4A and 4B show a pair of forming structures 101 wherein both forming structures 110,120 are rollers comprising protrusions 20, with the spaces between forming voids 30. In this embodiment, the protrusions 20 on each roller 108,109 are lined up so they engage.

In certain embodiments, the shapes of the protrusions 20 mimic the shapes of the voids 30. For instance, protrusions 20 and voids 30 may both be generally cylindrical and tapered and may have matching or different angles of taper. Or, in certain embodiments, the shapes of the protrusions 20 do not mimic the shapes of the voids 30. For example, protrusions 20 may be circular while voids 30 may be squared or oval. The forming elements 10 of the forming structures 110,120 can have a variety of different cross-sectional shapes, such as generally columnar or non-columnar shapes, including circular, oval, hour-glass shaped, star shaped, polygonal, and the like, and combinations thereof. Polygonal cross-sectional shapes include, but are not limited to, rectangular, triangular, hexagonal, or trapezoidal.

In general, the forming structures 110,120 for a given portion thereof will include at least about 200, at least about 220; from about 240 to about 10,000; from about 300 to about 5,000; or from about 350 to about 3,000 forming elements 10 per square centimeter. One objective of the present invention is that there is sufficient web tension and/or friction between the precursor web 50 and the forming structures 110,120 to allow the micro-textured web 60 formation to occur. The web 50 is held in place during micro-texturing by web tension and/or friction in the machine direction, cross direction, angle from the machine direction, or combination thereof.

Referring to FIG. 3, adjacent protrusions 20 have a center-to-center spacing C which can be controlled so as to control the spacing of the resulting discrete 3-D elements 62. At least one protrusion 28 has center-to-center spacings of less than about 800 microns with at least three, at least four, or at least five of its adjacent protrusions 20. In some embodiments, at least 25%, at least 50%, at least 75%, at least 95%, or all of the protrusions 20 on a forming structure have center-to-center spacings of less than about 800 microns with at least three, at least four, or at least five of their adjacent protrusions 20. Other acceptable center-to-center spacings are from about 30 microns to about 700 microns, from about 50 microns to about 600 microns, from about 100 microns to about 500 microns, or from about 150 microns to about 400 microns. Center-to-center spacings among adjacent protrusions 20 may be the same or different.

Forming elements 10 may be aligned in the machine direction, cross direction, or at an angle from the machine direction or cross direction. The forming elements 10 may be arranged in random arrays or non-random arrays. Examples of non-random arrays include rectangular, hexagonal, square, and combinations thereof. Arrays of forming elements 10 may be designed to increase the strength of the micro-textured web 60, for example, by minimal alignment in the machine direction, the cross direction strength will be increased. Arrays of forming elements 10 may be designed to maximize ease of tearing the micro-textured web 60, for example, with serrated or linear alignments.

Figure 11:
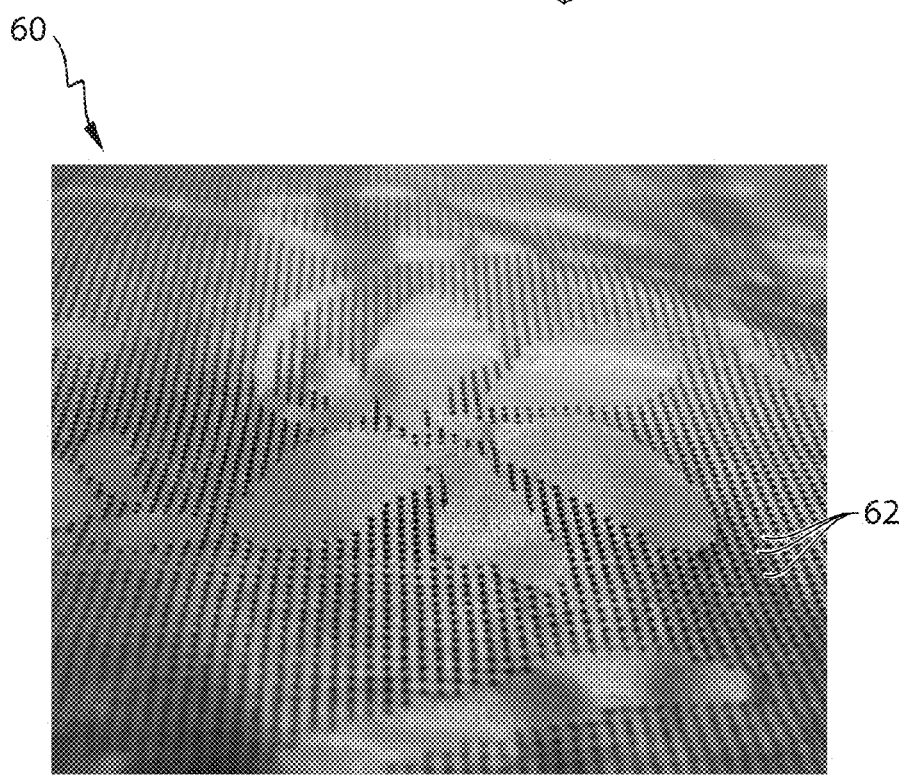
FIG. 11 shows a micro-textured web made by a process of the instant invention.

In certain embodiments, a portion of the forming structures 110,120 can include area densities of forming elements 10 as described above, while other portions of the forming structures 110,120 may include no forming elements 10, as shown in FIG. 9. The areas of the forming structures 110,120 having no forming elements 10 can be located at a different radial distance or in a different horizontal plane. In other embodiments, the forming elements 10 of the forming structures 110,120 can be located at a different radial distance or in different horizontal planes of the forming structures 110,120. The portions having no forming elements 10 and/or the portions having forming elements 10 located in different horizontal planes of the forming structures 110,120 can be in the form of a specific pattern or design, such as a flower, bird, ribbon, wave, cartoon character, logo, and the like, so that the micro-textured web 60 will have a portion that stands out visually from, and/or has a different hand feel when touched relative to, the remainder of the web. For example, the micro-textured web 60 can include a non-micro-textured portion that stands out visually from, and/or has a different hand feel from micro-textured portions, such as described in U.S. Pat. No. 5,158,819. Portions of forming structures 110,120 having no forming elements 10 do not factor into the center-to-center spacing requirements of adjacent forming elements in portions of forming structures 110,120 having forming elements 10. For instance, if two portions with forming elements are separated by a third portion without forming elements, forming elements from the first portion are not considered adjacent to forming elements from the second portion; only forming elements within each portion are considered adjacent to one another. An exemplary web 60 made by forming structures having portions with and without forming structures (e.g., as in FIG. 10B) is shown in FIG. 11.

Forming structures 110,120 can be made of any material or materials that can be formed to have forming elements 10 having the necessary dimensions to make a micro-textured web 60 and is dimensionally stable over process temperature and strain ranges experienced by forming structures 110, 120. Forming elements 10 are preferably made integrally with forming structures 110,120. That is, the forming structures 110,120 are made as an integrated structure, either by removing material or by building up material. For example, the forming structures 110,120 having the required relatively small scale forming elements 10 can be made by local, selective removal of material, such as by electroplating, fusing nano- or micro-beads, photo-polymerization, chemical etching, mechanical etching, or by ablating by use of high-energy sources such as electrical-discharge machines (EDM) or lasers, or by electron beam (e-beam), or by electrochemical machining (ECM). See U.S. Pat. No. 6,852, 475 and U.S. application Ser. No. 12/879,567 for examples of methods of making suitable forming structures 110,120. In one embodiment, the forming structures 110,120 may be constructed by angled teeth and grooves.

If the mated pair 101 of forming structures 110,120 both include protrusions 20 and voids 30, the discrete 3-D elements 62 can be formed in the micro-textured web 60 extending from the surface of the micro-textured web 60 opposite the surface from which the discrete 3-D elements 62 formed by the voids 30 of the forming structures 110,120 are formed. See, for example, FIGS. 4A and 4B. As a result, a two-sided micro-textured web 60 can be created, having different patterns or dimensions of 3-D elements 62 on each side of the micro-textured web 60. Depending upon the strain generated by the forming apparatus, as well as the geometric shapes of the voids 30 and optional pillars 24 of the forming structures 110,120, the discrete 3-D elements 62 of the micro-textured web 60 can have open, or apertured distal ends 67; closed distal ends 68; open, or apertured sidewalls 71, closed sidewalls 72, or chads 73. In addition, the sizes, shapes, and area densities of the 3-D elements 62 on one side of the two-sided micro-textured web 60 can be controlled independent of the other side of the two-sided micro-textured web 60.

Precursor Web

A precursor web 50 is converted into a micro-textured web 60 according to the process of the disclosure. Suitable precursor webs 50 include materials that can be deformed beyond their yield point by the strain put on the web in the deformation zone of the process, such that the precursor web 50 is forced to conform between the forming elements 10 of the forming structures 110,120 to produce a micro-textured web 60 having discrete three-dimensional elements ("3-D elements") 62, as shown in FIG. 11. Precursor webs 50 can comprise any suitable woven, nonwoven, film, combination or laminate of any of the foregoing materials. Non-limiting examples of suitable webs include cellulose, films, such as polymeric or thermoplastic films, foils, such as metallic foils (e.g. aluminum, brass, copper, and the like), webs comprising sustainable polymers, foams, fibrous nonwoven webs comprising synthetic fibers (e.g. TYVEK®), collagen films, chitosan films, rayon, cellophane, and the like. Suitable webs further include laminates or blends of these materials. Suitable films include both cast and blown. Precursor webs 50 can be similar to those described in U.S. application Ser. No. 12/879,567. The thickness of the precursor web 50 prior to micro-texturing will typically range from 5 to 150, 10 to 100, or 15 to 50 microns. Other suitable thicknesses include 10, 15, 20, 25, or 30 microns.

Thermoplastic precursor webs 50 will typically have a yield point and the precursor web 50 is preferably stretched beyond its yield point to form a micro-textured web 60. That is, the precursor web 50 should have sufficient yield properties such that the precursor web 50 can be strained without rupture to an extent to produce the desired discrete 3-D elements 62 with closed distal ends 68 or, in the case of a micro-textured web 60 comprising discrete 3-D elements 62 having open distal ends 67 or open sidewalls 71, rupture to form open distal ends 67 or open sidewalls 71. As disclosed below, process conditions such as temperature can be varied for a given polymer to permit it to stretch with or without rupture to form the micro-textured web 60 having the desired discrete 3-D elements 62. It has been found that preferred starting materials to be used as the precursor web 50 for producing the micro-textured web 60 exhibit low yield and high-elongation characteristics. Examples of films suitable for use as the precursor web 50 comprise low density polyethylene (LDPE), linear low-density polyethylene (LLDPE), and blends of linear low-density polyethylene and low density polyethylene (LLDPE/LDPE).

The process of the present invention may be used to make an article having an embossed seal including at least two precursor webs 50, and an embossed seal joining a portion of the at least two webs, the seal including co-registered concentric discrete 3-D elements formed in the at least two webs, the discrete 3-D elements having open proximal ends. See US 2010/0233428 and U.S. application Ser. No. 12/879, 531 for more on sealing film/film, film/nonwoven, and quiet seals.

The precursor web 50 can also optionally include colorants, such as pigment, lake, toner, dye, ink or other agent used to impart a color to a material, to improve the visual appearance of the micro-textured web 60. Suitable pigments herein include inorganic pigments, pearlescent pigments, interference pigments, and the like. Non-limiting examples of suitable pigments include talc, mica, magnesium carbonate, calcium carbonate, magnesium silicate, aluminum magnesium silicate, silica, titanium dioxide, zinc oxide, red iron oxide, yellow iron oxide, black iron oxide, carbon black, ultramarine, polyethylene powder, methacrylate powder, polystyrene powder, silk powder, crystalline cellulose, starch, titanated mica, iron oxide titanated mica, bismuth oxychloride, and the like. Suitable colored webs are described in US 2010/0233438 and US 2010/0233439. Precursor webs 50 can include various optional ingredients, such as those described in U.S. application Ser. No. 12/879, 567.

Micro-Textured Web

Figure 12A:
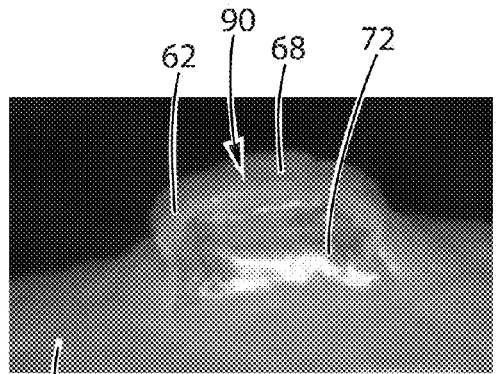
FIGS. 12A-E are examples of discrete three-dimensional elements.
Figure 12B:
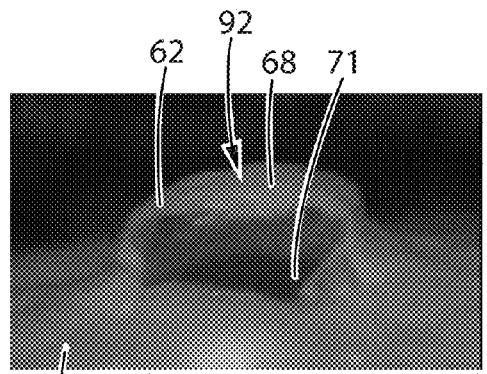
Figure 12C:
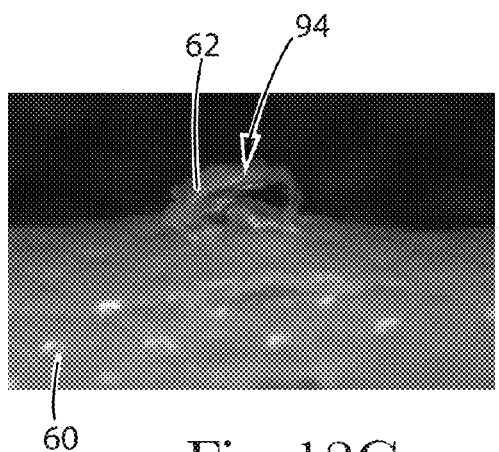
Figure 12D:
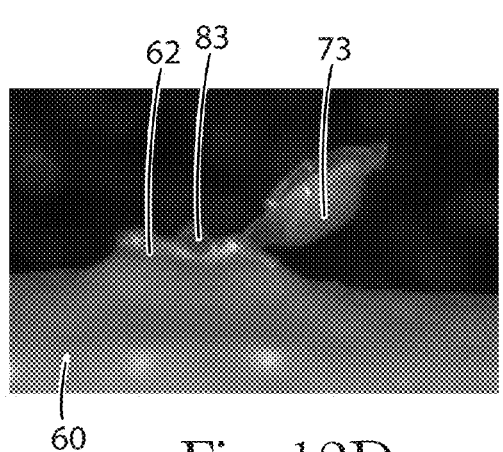
Figure 12E:
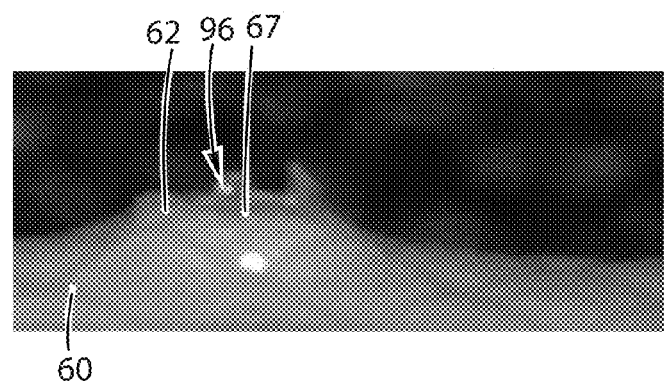
Figure 13:
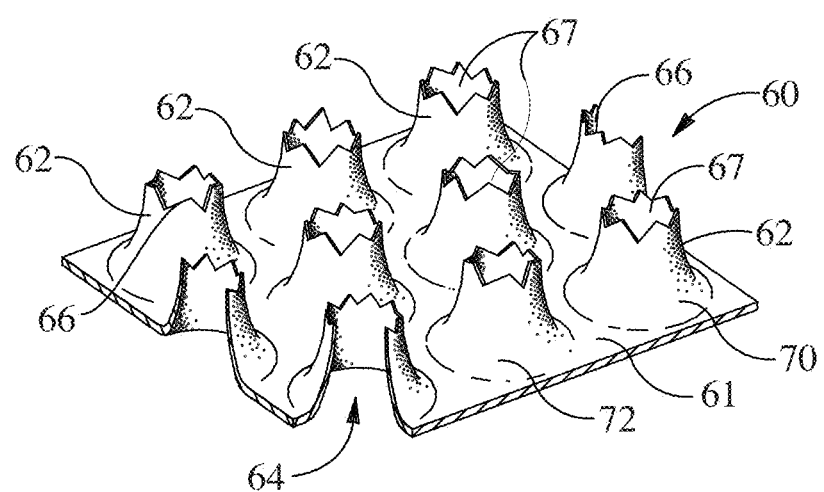
FIG. 13 is a perspective view of a portion of a web.
Figure 14:
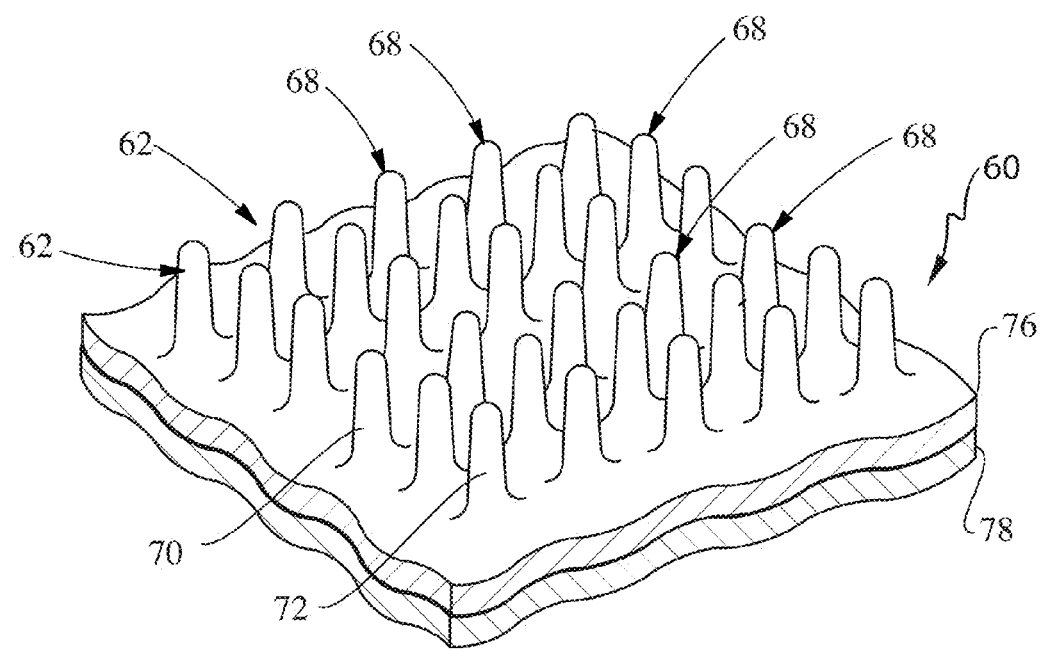
FIG. 14 is a perspective view of a portion of another web.

A precursor web 50 is processed according to the process of the disclosure to form a micro-textured web 60 that can have various desired structural features and properties such as desired soft hand feel, an aesthetically pleasing visual appearance, and improved sound effects (e.g., when handled or manually manipulated, the micro-textured web 60 may create less sound as compared to the precursor web 50). The precursor web 50 is positioned between the first forming structure 110 and the second forming structure 120. A pair of mated forming structures 101 is provided to conform the precursor web 50 between the forming elements of the first and second forming structures 110,120. A first micro-textured web 60 having discrete three-dimensional elements ("3-D elements") 62 is thereby produced. FIG. 11 shows an example of a micro-textured web 60 of the present invention. Exemplary discrete 3-D elements 62 are pictured in FIGS. 12A-E. FIG. 12A shows a bubble 90 wherein the sidewalls are thinned in the cross direction. FIG. 12B shows a hood 92, FIG. 12C a ribbon 94, FIG. 12D a chad 73, and FIG. 12E a crater 96. The discrete 3-D elements 62 are formed as protruded extensions of the web, generally on a first surface 76 thereof. The discrete 3-D elements 62 may have open proximal ends 64 and open 67 (e.g., FIG. 13) or closed 68 (e.g., FIGS. 14 and 15) distal ends.

The number, size, and distribution of discrete 3-D elements 62 on the micro-textured web 60 can be predetermined based on desired soft feel and visual effects. For applications such as a topsheet, backsheet or release paper wrapper in disposable absorbent articles, or packaging, it can be desired that the discrete 3-D elements 62 protrude only from one surface of micro-textured web 60. Therefore, when the micro-textured web 60 is used as a topsheet in a disposable absorbent article, the micro-textured web 60 can be oriented such that the discrete 3-D elements 62 are skin contacting for superior softness impression. Moreover, having discrete 3-D elements 62 with closed distal ends 68 can result in reduced rewet, i.e., reduced amounts of fluid being re-introduced to the surface of the topsheet after having been first passed through apertures of the topsheet to underlying absorbent layers. In other embodiments, it will be desired to have discrete 3-D elements 62 on both the first surface 76 and second surface 78 of the micro-textured web 60.

Figure 15:
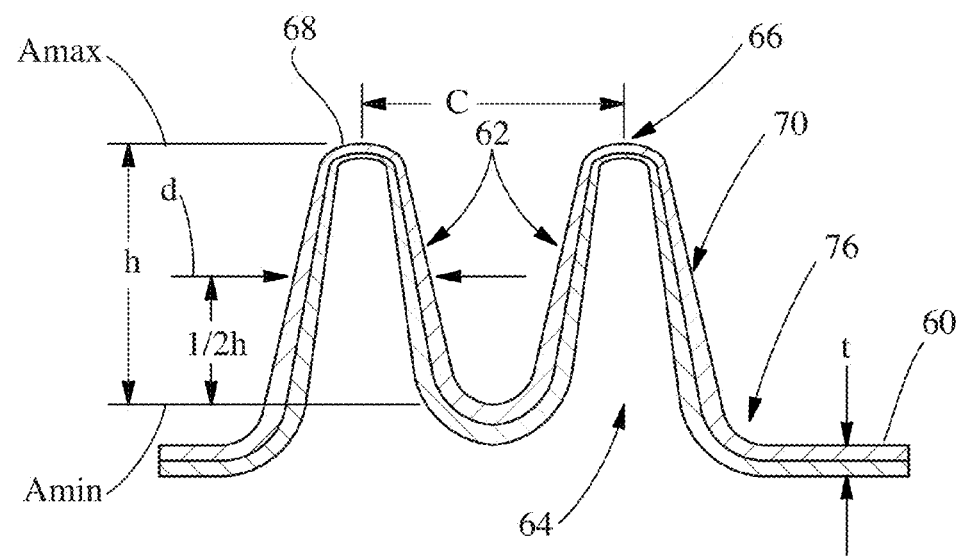
FIG. 15 is a cross-sectional view of exemplary three-dimensional elements.

Referring to FIG. 15, the discrete 3-D elements 62 can be described as protruding from a first surface 76 of the micro-textured web 60. As such, the discrete 3-D elements 62 can be described as being integral with web 60, and formed by permanent local plastic deformation of the precursor web 50. The discrete 3-D elements 62 can be described as having sidewalls 70 defining an open proximal portion 64 and an open 67 or closed 68 distal end 66. The discrete 3-D elements 62 each have a height h measured from a minimum amplitude $A_{min}$ between adjacent 3-D elements 62 to a maximum amplitude $A_{max}$ at the closed or open distal end 66. The discrete 3-D elements 62 have a diameter d, which for a generally cylindrical structure is the outside diameter at a lateral cross-section. By "lateral" is meant generally parallel to the plane of the first surface 76. For generally columnar discrete 3-D elements 62 having non-uniform lateral cross-sections, and/or non-cylindrical structures of discrete 3-D elements 62, diameter d is measured as the average lateral cross-sectional dimension at ½ the height h of the discrete three-dimensional element. Thus, for each discrete three-dimensional element, an aspect ratio, defined as h/d, can be determined. The discrete three-dimensional element can have an aspect ratio h/d of at least 0.2, at least 0.3, at least 0.5, at least 0.75, at least 1, at least 1.5, at least 2, at least 2.5, or at least 3. The discrete 3-D elements 62 will typically have a height h of at least 30 microns, at least 50 microns, at least 65 microns, at least 80 microns, at least 100 microns, at least 120 microns, at least 150 microns, or at least 200 microns. The 3-D elements 62 will typically be at least the same height as the thickness of the precursor web 50, or at least two times the thickness of the precursor web 50, or preferably at least three times the thickness of the precursor web 50. The discrete 3-D elements 62 will typically have a diameter d of 50 microns to 790 microns, 50 microns to 600 microns, 50 microns to 500 microns, 65 microns to 400 microns, or 75 microns to 300 microns. For discrete 3-D elements 62 that have generally non-columnar or irregular shapes, a diameter of the discrete three-dimensional element can be defined as two times the radius of gyration of the discrete three-dimensional element at ½ height.

In one embodiment, the diameter of a discrete three-dimensional element is constant or decreases with increasing amplitude (amplitude increases to a maximum at closed or open distal end 66). The diameter, or average lateral cross-sectional dimension, of the discrete 3-D elements 62 can be a maximum at proximal portion and the lateral cross-sectional dimension steadily decreases to distal end. This structure 110,120 is desirable to help ensure the micro-textured web 60 can be readily removed from the forming structures 110,120.

Figure 16A:
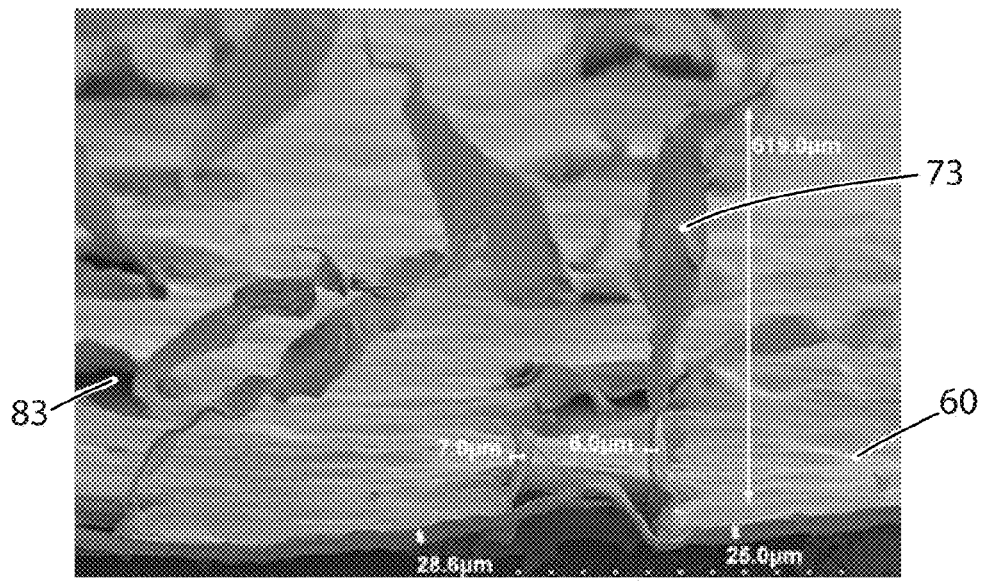
FIGS. 16A and 16B are images of three-dimensional elements comprising chads.
Figure 16B:
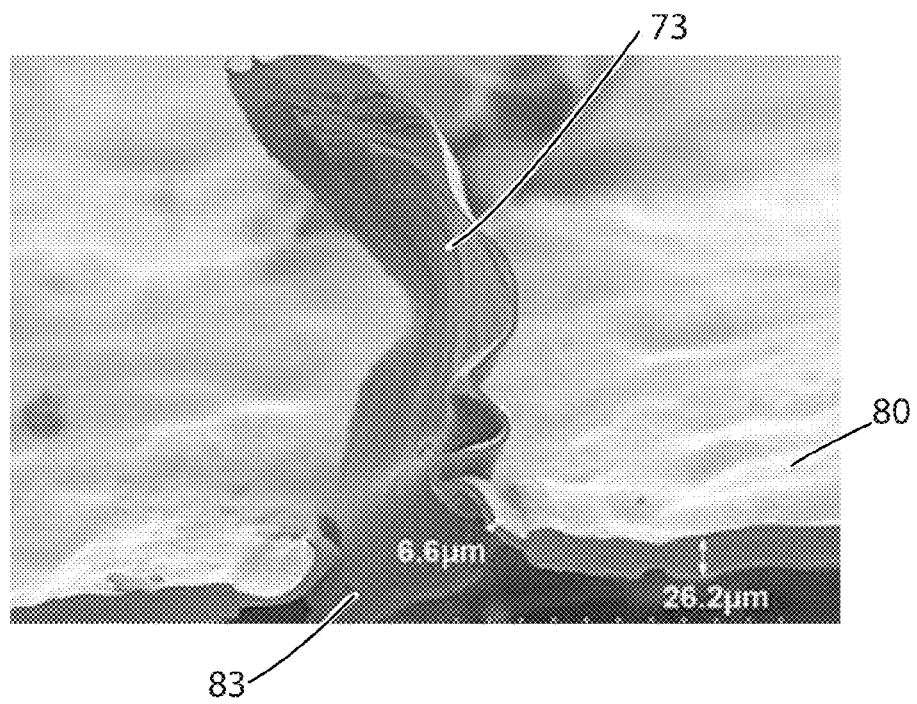

Thinning of the precursor web 50 can occur due to the relatively deep drawing required to form high aspect ratio discrete 3-D elements 62. For example, thinning can be observed at the closed 68 or open 67 distal ends 66 and/or along the sidewalls 70. By "observed" is meant that the thinning is distinct when viewed in magnified cross-section. Such thinning can be beneficial as the thinned portions offer little resistance to compression or shear when touched. For example, when a person touches the micro-textured web 60 on the side exhibiting discrete 3-D elements 62, the fingertips of the person first contact the closed or open distal ends 67 of the discrete 3-D elements 62. Due to the high aspect ratio of the discrete 3-D elements 62, and the wall thinning of the precursor web 50 at the distal ends 66 and/or along the sidewalls 70, the discrete 3-D elements 62 offer little resistance to the compression or shear imposed on the micro-textured web 60 by the person's fingers. This lack of resistance is registered as a feeling of softness, much like the feeling of a velour fabric. A feeling of softness is achieved when the discrete 3-D elements 62 comprise chads 73 (and associated apertures 83), formed when the sidewalls 70 thin and rupture, leaving an aperture 83 and a flap of web material, or chad 73, attached to a web, as depicted in FIGS. 16A (web 60) and 16B (web 80).

Thinning of the precursor web 50 at the distal ends 66 and/or along the sidewalls 70 can be measured relative to the thickness of the precursor web 50 or relative to the thickness of the land area 61 that completely surrounds the discrete 3-D elements 62 of the micro-textured web 60. The precursor web 50 will typically exhibit thinning of at least 25%, at least 50%, or at least 75% relative to the thickness of the precursor web 50. The precursor web 50 will typically exhibit thinning of at least 25%, at least 50%, at least 75%, or at least 85% relative to the thickness of the land area surrounding the discrete 3-D elements 62 of the micro-textured web 60. In some embodiments, there is relatively little thinning at the distal end 66, such as when using protrusions 20 which are not relatively sharp. In such instances, it is believed that friction lock occurs, leading to relatively more thinning on the sidewalls 70.

The "area density" of the discrete 3-D elements 62, which is the number of discrete 3-D elements 62 per unit area of first surface 76, can be optimized and the micro-textured web 60 will typically include about 200 to about 3,000; or about 200 to about 10,000; about 220 to 8,000; about 240 to about 6,000; about 300 to about 5,000; or about 350 to about 3,000 discrete 3-D elements 62 per square centimeter. In general, the center-to-center spacing can be optimized for adequate tactile impression, while at the same time minimizing entrapment of materials, such as fluids, between discrete 3-D elements 62 when the web is used as a topsheet. Referring back to FIG. 15, the center-to-center spacing C between adjacent discrete 3-D elements 62 can be about 100 microns to about 800 microns, about 140 microns to about 650 microns, about 180 microns to about 600 microns, or about 250 microns to about 550 microns.

Figure 17:
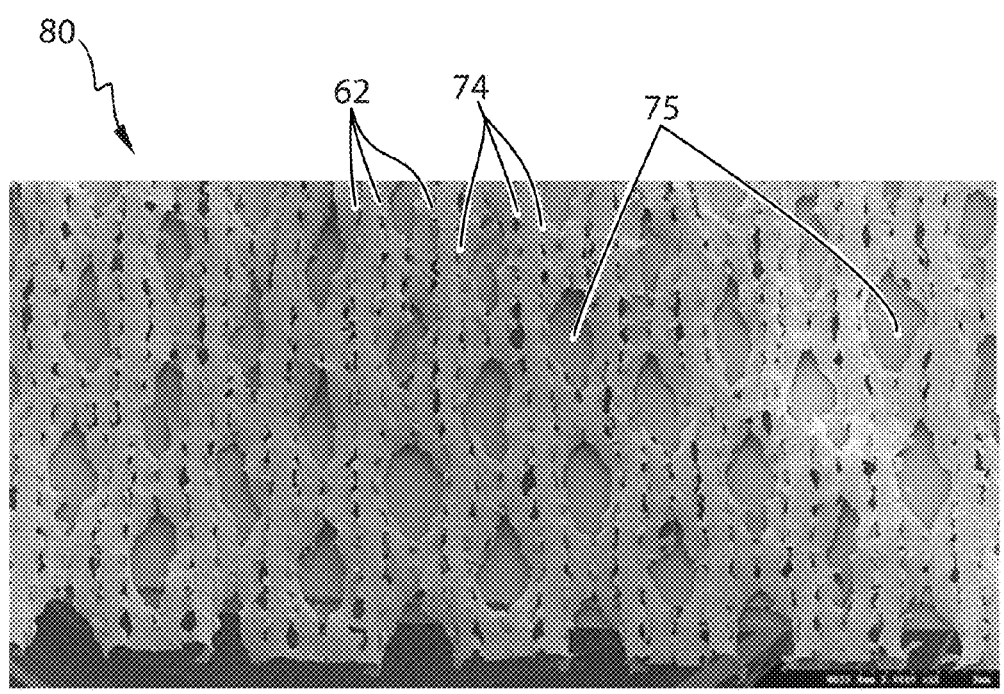
FIG. 17 shows a second web made by a process of the instant invention.
Figure 19:
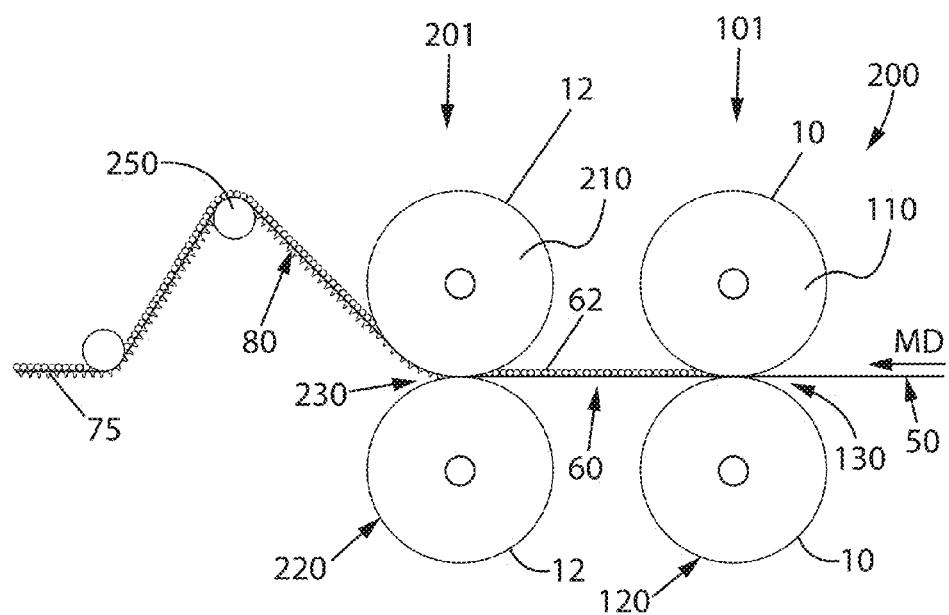
FIG. 19 is a perspective view of another forming process.

A second micro-textured web 80 having second discrete 3-D elements 74, third discrete 3-D elements, and/or macro 3-D elements 75 in addition to the first discrete 3-D elements 62 may be produced, as described below and shown in FIGS. 17 and 19. The second discrete 3-D elements 74 and/or macro 3-D elements 75 can be formed adjacent to, in between, or at least partially overlapping with, the first discrete 3-D elements 62. The first discrete 3-D elements 62, second discrete 3-D elements 74, and/or macro 3-D elements 75 can have various combinations of open and closed distal ends. Or, in other embodiments, the micro-textured web 60 resulting from the process described herein can have a generally non-apertured structure similar to that described in detail in U.S. Pat. No. 7,402,723 or U.S. Pat. No. 7,521,588. US 2010/0036338 A1 provides other webs which may be combined with the webs herein.

Process for Making Micro-Textured Web

As mentioned above, the micro-texturing process of the present invention comprises at least one pair of mated forming structures 101. The forming structures may comprise rollers, plates, belts, sleeves, or the like, or combinations thereof. Suitable pairs of forming structures 101 include, but are not limited to: a pair of counter-rotating rollers that define a nip therebetween, a pair of plates, a pair of belts, or the like.

Figure 18:
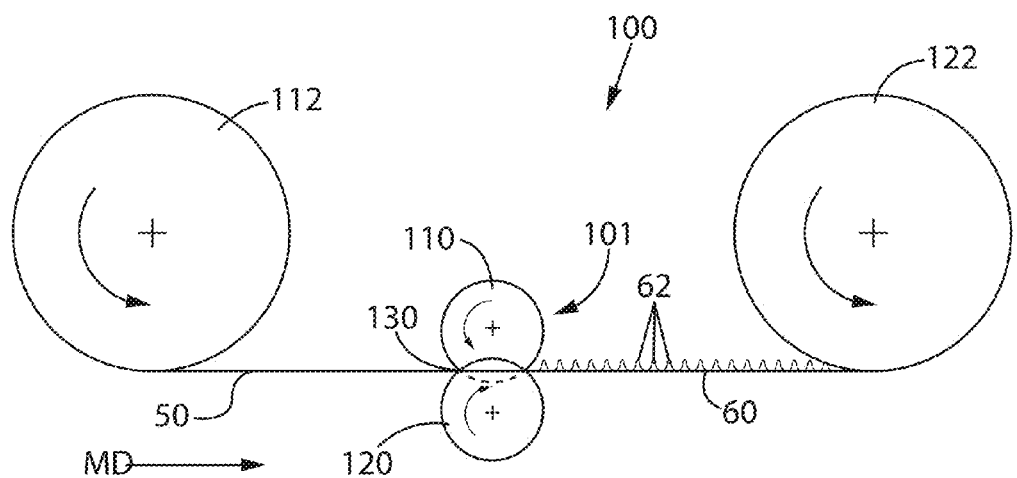
FIG. 18 is a perspective view of a forming process.

As shown in FIG. 18, a process 100 for forming a micro-textured web 60 includes moving a precursor web 50 from a first supply roll 112 through a pair of mated forming structures 101 to a rewind roll 122. The pair of forming structures 101 comprises a first forming structure 110 and a second forming structure 120 which mate at a deformation zone 130. In a preferred embodiment, at least the first forming structure 110 comprises voids 30 and at least the second forming structure 120 comprises protrusions 20. The precursor web 50 is moved through the deformation zone 130 between the two forming structures. In the deformation zone 130, the protrusions on the second forming structure 120 mate, or engage, with the voids on the first forming structure. The forming structures 110,120 engage at an engagement position 140 and have a depth of engagement DOE wherein there is an acceptable sidewall clearance 42 and tip-to-valley clearance 44 between protrusions 20 and voids 30, for example, as shown in FIGS. 7A-D. At the engagement position 140, at least a majority of the engaged voids and protrusions are separated from each other by a sidewall clearance 42 ranging from about 30 microns to about 300 microns and a tip-to-valley clearance 44 of greater than 30 microns. Typically, the sidewall angle of the protrusions 20 are defined such that when the forming structures engage, there is sufficient clearance for the web and the web is not sheared (where portions of the web forced to slip relative to other portions) or pinched by the forming structures. The rolls 110,120 may rotate at substantially the same speed as the speed at which the web is fed through the nip between the rolls; or, they may rotate at a greater or lesser speed than the speed at which the web is fed through the nip between the rolls.

The forces in the deformation zone 130 upon the precursor web 50 are sufficient to cause the precursor web 50 to conform to the forming elements 10 to form a micro-textured web 60 having discrete three-dimensional elements ("3-D elements") 62. The conformation of the precursor web 50 to the forming elements 10 can be partial, substantial, or complete conformation (unless rupture occurs), depending upon the precursor web 50, the strain induced on the precursor web 50, the temperature, and the topography of the forming structures 110,120.

The micro-texturing process can optionally be combined with other processes to further manipulate the micro-textured web 60. For example, as shown in FIG. 19, a micro-textured web 60 may go through at least a second deformation zone 230 to form a second micro-textured web 80. Additional webs may be introduced to the process at any time. The forces in the deformation zone 230 upon the first micro-textured web 60 are sufficient to cause the first micro-textured web 60 to conform to the second forming elements 12 to form a second micro-textured web 80 having second discrete 3-D elements 74 and/or macro 3-D elements 75 as well as the first discrete 3-D elements 62 (or some deformed variation of them). The macro 3-D elements 75 may have an area of greater than 0.6 mm$^2$, or from 0.8 mm$^2$ to 5 mm$^2$, 1 mm$^2$ to 4 mm$^2$, or 1.5 mm$^2$ to 3 mm$^2$. Macro 3-D elements 75 shown in FIG. 17 were made according to US 2006/0087053 A1. The conformation of the first micro-textured web 60 to the second forming elements 12 can be a partial, substantial, or complete conformation, depending upon the precursor web 60, the strain induced on the web 60, the temperature, and the topography of the forming structures 210,220. A shadow effect of a pattern can be created using a first pair and second pair of forming structures 101,201 having aligned portions having no forming elements 10 and controlling the location of the first micro-textured web 60.

Figure 20A:
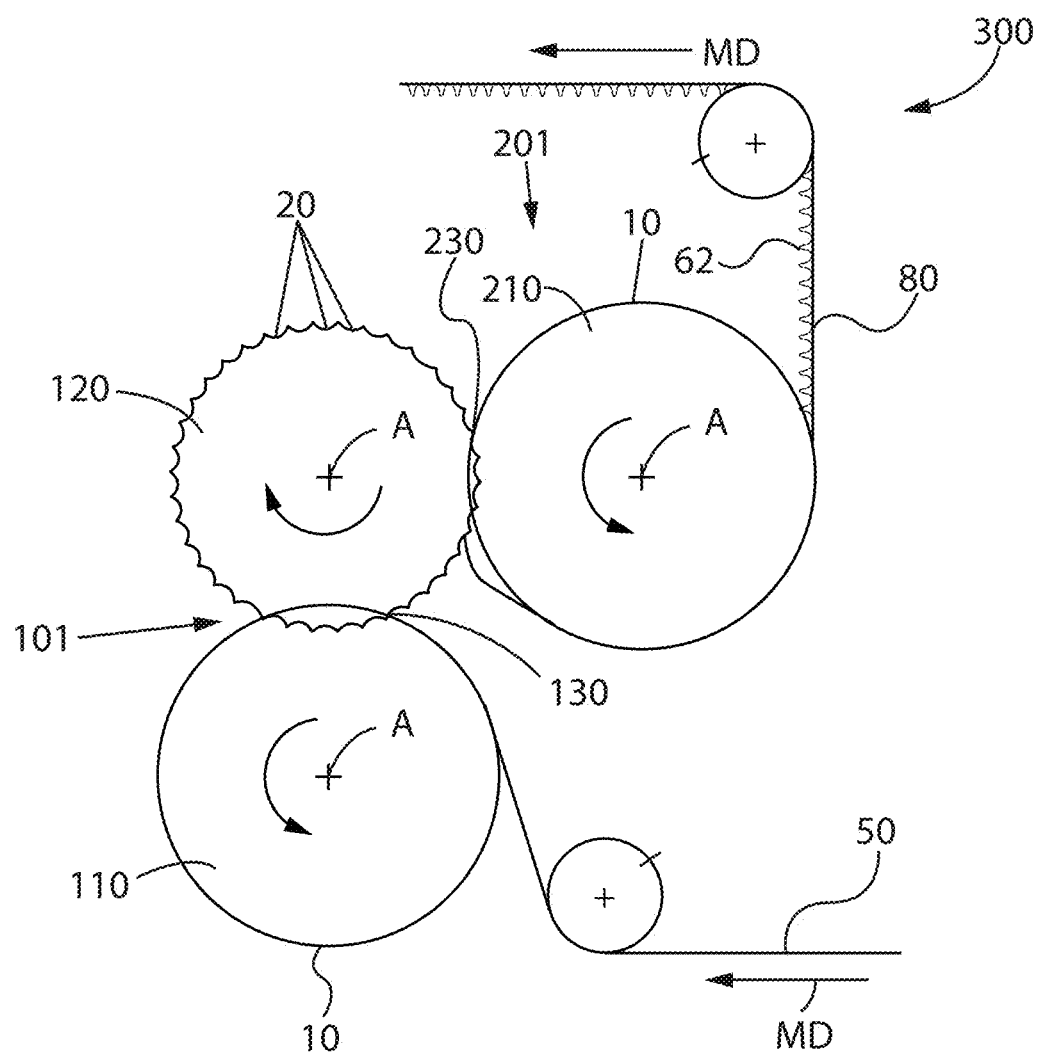
FIGS. 20A and 20B are perspective views of forming processes.
Figure 20B:
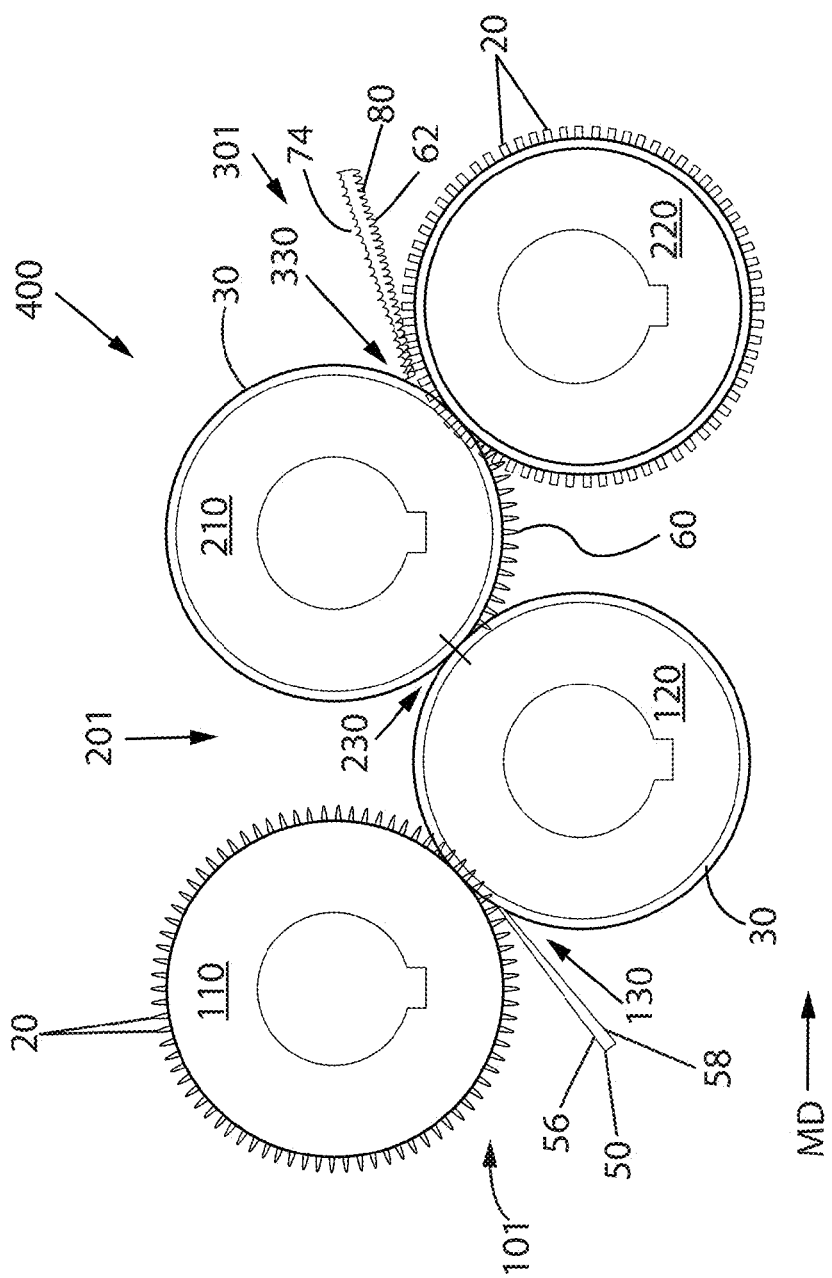

The second pair of mated forming structures 210,220 may comprise third and fourth forming structures separate from the first and second forming structures. As shown in FIG. 19, the two deformation zones, or nips, 130,230 are separated in space. Alternatively, a second deformation zone 230 can be created by a third forming structure 210 if it is nested with or mated to either of the first or second forming structures 110,120. For example, in the process 300 shown in FIG. 20A, forming structures 110,210 can be mated with forming structure 120 in a planetary arrangement. Forming structures 110,210 have at least some forming elements 10 in a similar size and/or array so as to mate with second forming structure 120. If the web 60 is still registered on the same forming structure/protrusions 20, as shown in FIG. 20A, the second deformation zone 230 may yield a greater degree of conformation of the web 60 to at least some of the forming elements 10 (everywhere or in certain locations). If the web 60 is not registered on the same forming structure/protrusions, as shown in the nested arrangement of FIG. 20B, the second deformation zone 230 or third deformation zone 330 may increase area density of the discrete 3-D elements with cheaper tooling and at faster line speeds as well as create a web 80 having first and second discrete 3-D elements 62,74 extending from both sides of the web. For examples, see U.S. application Ser. No. 12/879,567 and U.S. patent application Ser. No. 13/094,206, "Method for Deforming a Web", to Orr filed on the same date as the present application.

While not being bound by theory, it is believed that factors such as the precursor web 50; the shape, size, variety, and center-to-center spacing of the protrusions 20 and voids 30; the strain induced on the precursor web 50; the temperature; and the topography of the forming structures 110,120; as well as the strain applied can be adjusted to produce a desired web 60 having, e.g., discrete 3-D elements 62 on one or both sides of the web 60, with closed or open distal ends 66 or closed or open sidewalls 70, etc. To obtain permanent deformation of the precursor web 50 and the first micro-textured web 60 to form the first micro-textured web 60 and the second micro-textured web 80, respectively, the strain applied is generally sufficient to stretch the precursor beyond its yield point. Different levels of strain may be induced by varying the depth of engagement between the two forming structures 110,120.

The process can have relatively short dwell times. Dwell time refers to the amount of time strain is applied to a given portion of the precursor web 50 or the first micro-textured web 60, usually the amount of time a given portion of the precursor web 50 or the first micro-textured web 60 spends positioned in the deformation zone, or nip 130,230,330 between pairs of forming structures 101,201,301. Strain is typically applied to the precursor web 50 or the first micro-textured web 60 for a dwell time of less than 5 seconds, less than 1 second, less than 0.5 second, less than 0.1 second, less than 0.01 second, or less than 0.005 second. For example, the dwell time can be 0.5 milliseconds to 50 milliseconds. Strain can be applied to the precursor web 50 during a first deformation zone 130 for a first dwell time and strain can be applied to the first micro-textured web 60 during a second deformation zone 230 for a second dwell time. The first and second dwell times can be substantially equal or can be different. Even with such relatively short dwell times, micro-textured webs can be produced with desirable structural features described herein. As a result, the process of the disclosure enables high speed production of micro-textured webs. In other embodiments, the process can have relatively long dwell times, such as the method for incrementally stretching a web, described in US 2008/0224351.

The precursor web 50 or the first micro-textured web 60 can be fed between the first and second forming steps at a rate of at least 0.01 meters per second, at least 1 meter per second, at least 5 meters per second, or at least 10 meters per second. Other suitable rates include, for example, at least 0.01, 0.05, 0.1, 0.5, 1, 2, 3, 4, 5, 6, 7, 8, 9, or 10 meters per second. The rate at which the precursor web 50 is fed between the first pair of forming structures 101 can be substantially the same or different as the rate the first micro-textured web 60 is fed between the second pair of forming structures 201.

Any or each of the micro-texturing steps of the process can be carried out at ambient temperature, meaning that no heat is intentionally applied to the forming structures and/or webs. It should be recognized, however, that heat can be generated due to the high strain of the precursor web 50. As a result, the forming structures may be cooled in order to maintain the process conditions at the desired temperature, such as ambient temperature. Any or each of the micro-texturing steps of the process can also be carried out with the web having an elevated temperature. For example, the temperature of the web can be less than the melting point of the precursor web 50. For example, the temperature of the web can be at least 10° C. below the melting point of the precursor web 50. In general, the process can be carried out at a temperature of from 10° C. to 200° C., from 10° C. to 120° C., from 10° C. to 80° C., or from 10° C. to 40° C. The web 50 can be heated by a preheating step or by actively heating one or both of the forming structures. The temperature can be measured by, for example, a non-contact thermometer, such as an infrared thermometer or a laser thermometer, measuring the temperature at the deformation zone 130,230. The temperature can also be determined using temperature sensitive material such as Thermolabel available from Paper Thermometer Company.

Figure 21A:
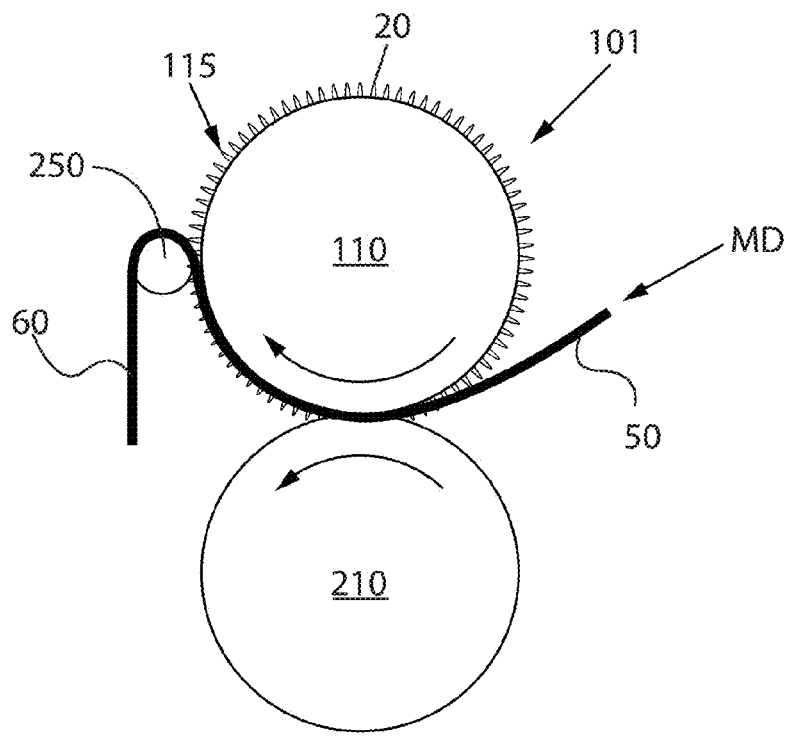
Figure 21B:
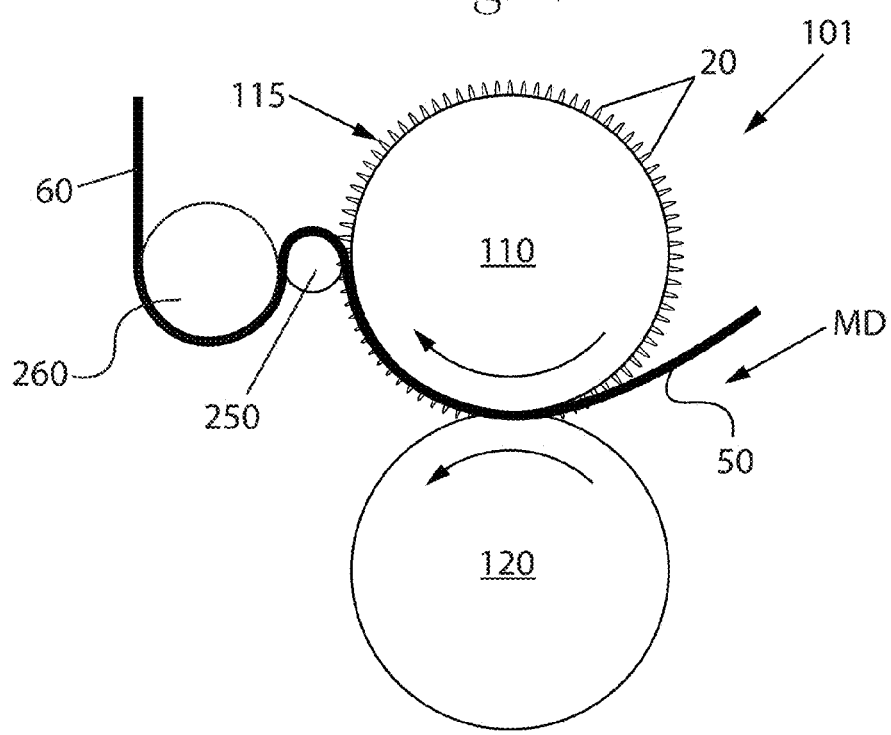

As shown in FIGS. 21A-E, the process may include mechanisms to aid release of the formed web 60,80 from the forming structures 110,120. A stripping idler roll 250 may be positioned after the last pair of mated forming structures 101 (FIG. 21A). The stripping idler roll 250 is less than 50 mm, less than 40 mm, less than 30 mm, less than 20 mm, or less than 10 mm in diameter; preferably, the roll 250 is from 15 mm to 35 mm in diameter. It is desirable to position the stripping idler roll 250 as close as possible to the forming surface 115; the roll 250 may be positioned less than 5 mm, less than 4 mm, less than 3 mm, less than 2 mm, or less than 1 mm away from the forming surface 115. For best release, the angle of removal of the web 60 to the stripping idler roll 250 (the outfeed wrap angle) is greater than 90°, greater than 135°, or greater than 180° from the web interface point with the forming surface 115. Removal in a more positive way, such as with power-driven (FIG. 21B) or vacuum (FIGS. 21C-E) stripping rolls 250, further facilitates web release from the forming surface 115. FIG. 21B shows a stripping idler roll 250 having a small diameter and a 180° wrap angle. Positioned next to the roll 250 is a power-driven roller 260. Powered stripping may comprise a positive drive with short span length to protrusion release. The web 60 does not act as a variable spring in providing stripping tension. FIG. 21C shows a generic vacuum stripping concept wherein a vacuum source 270 is positioned next to the stripping idler roll 250. Additional force is created with the vacuum 270 to peel the web 60 from the forming surface 115. FIG. 21D shows a vacuum stripping option wherein the stripping roll 250 comprises a vacuum 270 and an internal, zoned plenum 280 (to minimize air requirements) for the area of the roll 250 covered by the web 60. FIG. 21E shows another vacuum stripping option wherein the stripping roll 250 comprises a vacuum 270 but no internal plenum; the small diameter roll 250 and high wrap angle minimize air requirements.

The process can optionally further include applying a slip agent to the precursor web 50 and/or the forming structures 110,120 before the precursor web 50 is provided between the forming structures 110,120 and the strain source. This can be beneficial, especially in a continuous process, to reduce friction and enhance release between the precursor web 50 and the forming structures and/or to minimize or eliminate inversions of the discrete 3-D elements 62. Non-limiting examples of suitable slip agents include silicone, talc, lubricating oils, and the like. Optionally, a renewable release agent can be used such as disclosed in U.S. Pat. No. 6,773,647.

The process can optionally include applying a positive pressure to the micro-textured web 60 to reinvert discrete 3-D elements 62 that may have inverted during removal of the micro-textured web 60 from the forming structures. The inverted discrete 3-D elements 62 can be reinverted to extend from the micro-textured web first surface 76 by applying a positive pressure, such as from an air knife, sufficient to reinvert the inverted discrete 3-D elements 62.

Uses of Micro-Textured Web

Micro-textured webs of the present invention can be utilized in a number of different ways, such as component materials of absorbent articles (such as topsheets, backsheets or release paper wrappers, e.g., for a feminine hygiene article, diaper, or adult incontinence article), packaging (such as flow wrap, shrink wrap, or polybags), trash bags, food wrap, wipes, electronic components, wall paper, clothing, window coverings, placemats, book covers, and the like.

EXAMPLES

Example 1

A micro-textured web 60 may be produced using flat plate forming structures 110,120. The first forming structure 110 includes about 440 apertures 34 per square centimeter. The second forming structure 120 includes about 440 pillars 24 per square centimeter. The forming elements of the forming structures 110,120 are arranged in a regular hexagonal array by laser engraving Delrin™ as generally disclosed in US 2010/0230858 A1. The pillars 24 of forming structure 120 have a circular cross-section with a diameter of about 152 microns and a center-to-center spacing of about 508 microns. The pillars 24 have a height of about 262 microns, straight sidewalls with a slight inward taper angle of about 5 degrees and the tips are rounded with a radius of about 45 microns. The apertures 34 of forming structure 110 have a circular cross-section with a diameter of about 178 microns and a center-to-center spacing of about 508 microns. The sidewall clearance between the pillars 24 and the apertures 34 is about 20 microns at an engagement of 400 microns. The precursor web 50 utilized is a polyethylene film having a fine square embossed pattern, obtained from the RKW-Group, Germany, that is about 25 microns thick and has a basis weight of about 24 gsm.

Figure 22A:
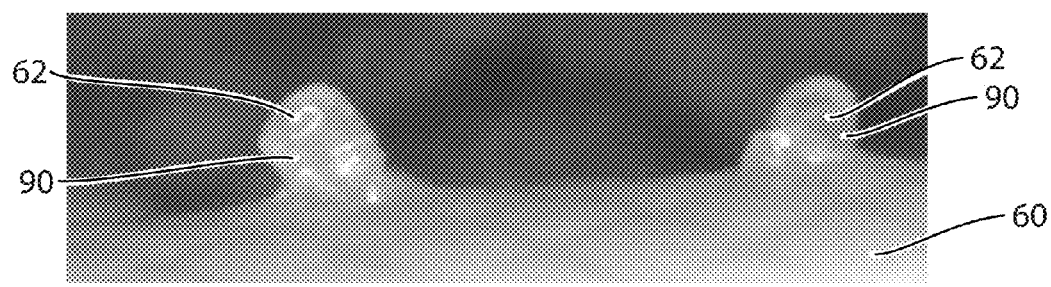
FIGS. 22A and 22B illustrate the micro-textured webs of Examples 1 and 2.

The micro-texturing process is performed using a high-speed research press (HSRP) at room temperature. The HSRP (described in detail in US 2009/0120308) is designed to simulate a continuous production line process for texturing the precursor web 50. The HSRP is operated to simulate forming structure 110,120 roll diameters of 206 mm. The precursor web 50 is fed between the forming structures 110,120 at a simulated rate of about 7.3 m/sec. An engagement of 400 microns is used. FIG. 22A illustrates a resultant micro-textured web 60 which includes a plurality of discrete three-dimensional elements 62 in the form of bubbles 90 with heights of about 100 microns. The fine square embossed pattern of the precursor web 50 is still apparent.

Example 2

A micro-textured web 60 may be produced using flat plate forming structures 110,120. The first forming structure 110 includes about 440 apertures 34 per square centimeter. The second forming structure 120 includes about 440 pillars 24 per square centimeter. The forming elements of the forming structures 110,120 are arranged in a regular hexagonal array by laser engraving Delrin™ as generally disclosed in US 2010/0230858 A1. The pillars 24 of forming structure 120 have a circular cross-section with a diameter of about 152 microns and a center-to-center spacing of about 508 microns. The pillars 24 have a height of about 262 microns, straight sidewalls with a slight inward taper angle of about 5 degrees and the tips are rounded with a radius of about 45 microns. The apertures 34 of forming structure 110 have an oval cross-section with a first diameter of about 188 microns and a second diameter of about 330 microns and a center-to-center spacing of about 508 microns. The long direction of the ovals are orientated in line with the shortest center-to-center distance lines between adjacent pillars of the mating forming structure 120. The first sidewall clearance between the pillars and the apertures is about 20 microns and a second sidewall clearance of about 80 microns at an engagement of 400 microns. The precursor web 50 used is a polyethylene film having a fine square embossed pattern, from the RKW-Group, Germany (about 25 microns thick; basis weight of about 24 gsm).

Figure 22B:
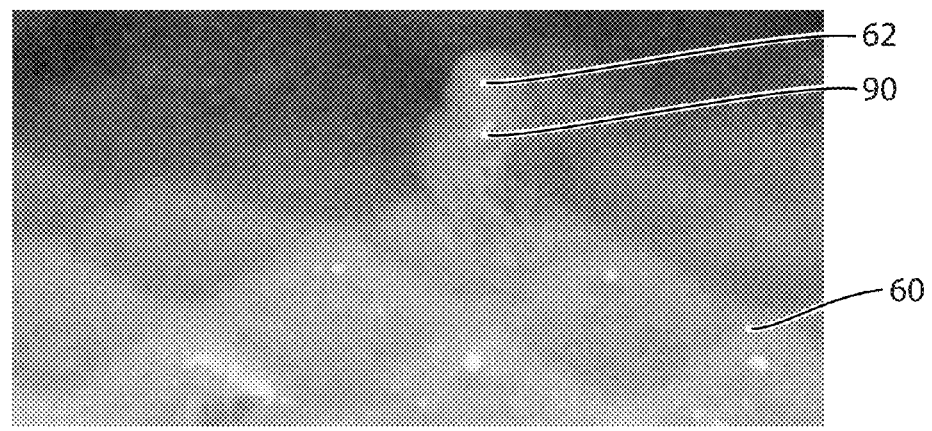

The micro-texturing process is performed using a high-speed research press (HSRP) at room temperature. The HSRP (described in detail in US 2009/0120308) is designed to simulate a continuous production line process for texturing the precursor web 50. The HSRP is operated to simulate forming structure 110,120 roll diameters of 206 mm. The precursor web 50 is fed between the forming structures 110,120 at a simulated rate of about 7.3 m/sec. An engagement of 400 microns is used. The resultant micro-textured web 60 includes a plurality of discrete three-dimensional elements 62 in the form of bubbles 90 with heights of about 100 microns, e.g., as shown in FIG. 22B. The fine square embossed pattern is still apparent.

Example 3

Figure 23A:
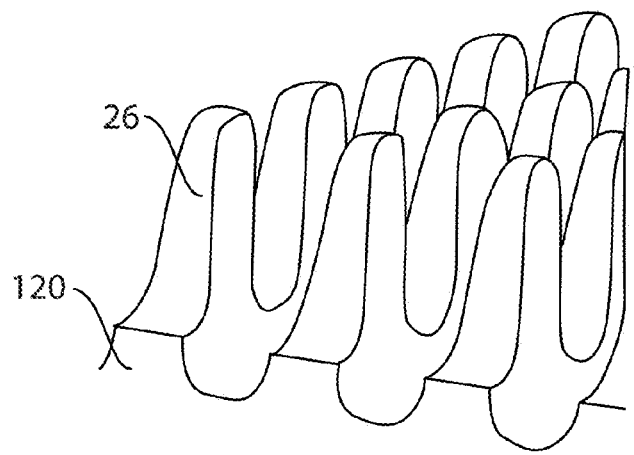
FIGS. 23A-C illustrate the teeth of Examples 3, 4, and 5.
Figure 23B:
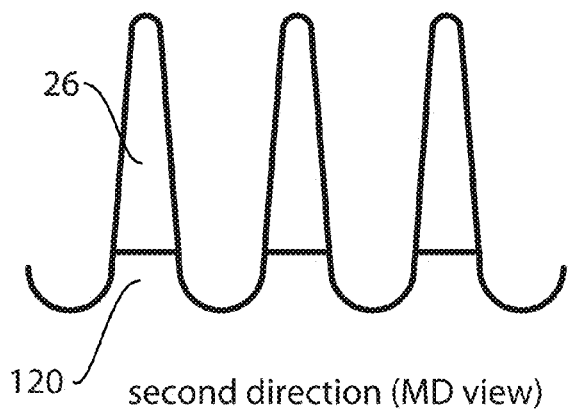
Figure 23C:
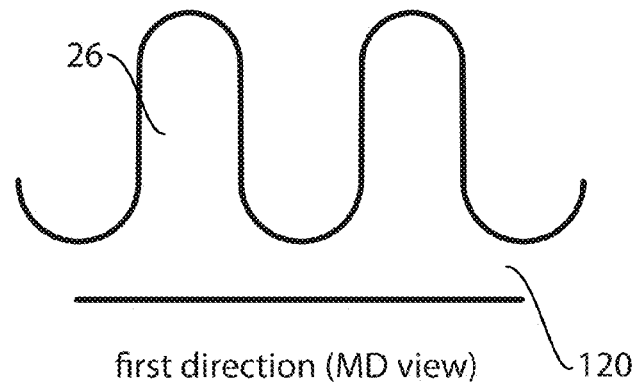

A micro-textured web 60 may be produced using flat plate forming structures 110,120. The first forming structure 110 includes parallel continuous grooves 39 and parallel ridges 28 running in a first direction, with a center-to-center spacing of about 520 microns in a second direction. The ridges 28 have a taper angle of about 5 degrees from vertical. The grooves 39 have a depth of about 940 microns and a diameter at half-depth of about 320 microns. The second forming structure 120 includes about 320 teeth 26 per square centimeter, the teeth 26 having a general shape as shown in FIGS. 23A-C. The teeth 26 are arranged in a rectangular array, with a center-to-center spacing of about 610 microns in a first direction and about 520 microns in a second direction. The teeth 26 have straight, vertical sidewalls in the first direction and tapered inward at an angle of about 10 degrees in the second direction. The teeth 26 have a height of about 610 microns in the first direction, about 800 microns in the second direction, and a rectangular cross section with a first diameter of about 230 microns and a second diameter of 130 microns at half-height. The tips are rounded with a first radius of about 115 microns and a second radius of about 50 microns. The forming structures 110,120 are made from aluminum by EDM wire engraving.

The precursor web 50 utilized is a polyethylene film having a fine square embossed pattern, obtained from the RKW-Group, Germany, that is about 18 microns thick and has a basis weight of about 17 grams per square meter (gsm).

The micro-texturing process is performed using a high speed research press (HSRP) at room temperature. The HSRP (described in detail in U.S. 2009/0120308) is designed to simulate a continuous production line process for embossing the precursor web 50. The HSRP is operated to simulate forming structure 110,120 roll diameters of 206 mm. The precursor web 50 is fed between the forming structures 110,120 in a pre-strained state of 1.5% in a first direction (parallel with the grooves and ridges) at a simulated rate of about 6 m/sec. The engagement is about 600 microns, at which point the sidewall clearances are about 105 microns in the second direction and the tip to valley clearance is about 330 microns.

Figure 24A:
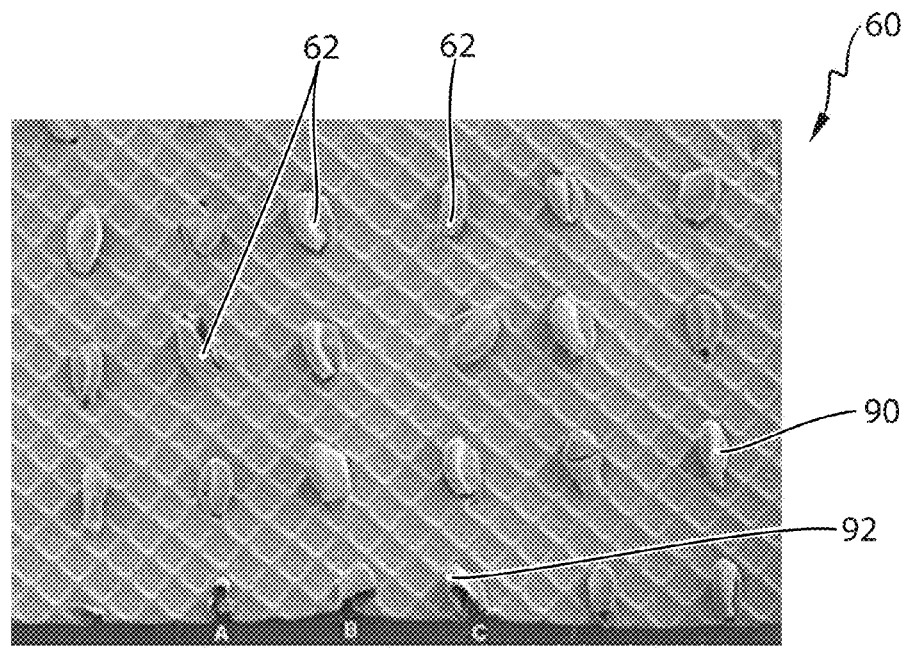
FIGS. 24A and 24B illustrate the micro-textured web of Example 3.
Figure 24B:
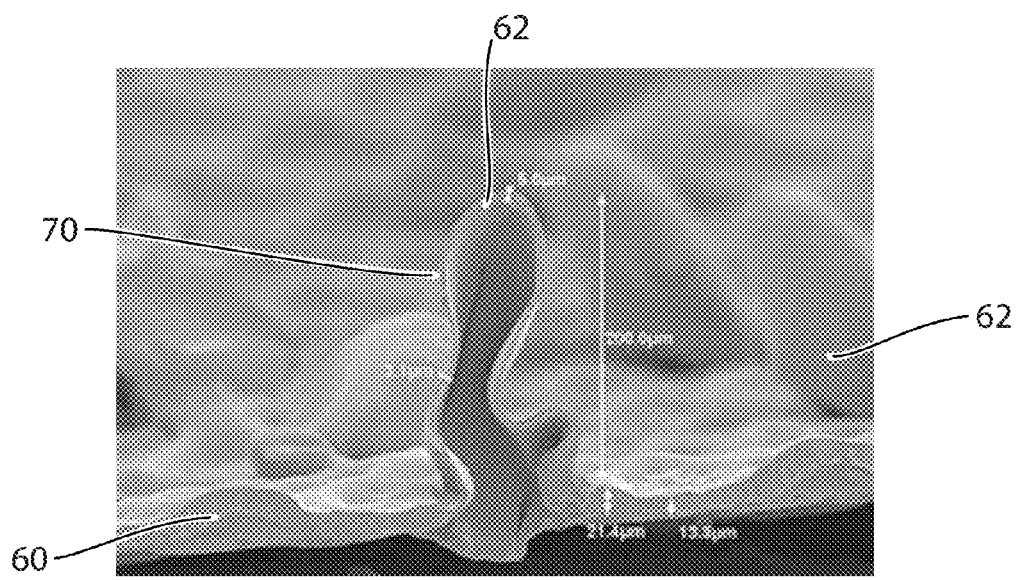

FIGS. 24A and 24B are SEM images which illustrate a resultant micro-textured web 60 which includes a plurality of discrete three-dimensional elements 62. The fine square embossed pattern of the precursor web is still apparent. The discrete 3-D elements 62 are predominantly in the form of bubbles 90 and some hoods 92 with significant sidewall and tip thinning. Heights of the discrete 3-D elements 62 are about 165 microns with a first diameter at half-height of about 220 microns and a second diameter at half-height of about 108 microns. FIG. 24B is a higher magnification cross-section side view of discrete 3-D element 62 labeled as A in FIG. 24A.

Example 4

A micro-textured web 60 may be produced on an apparatus similar to that shown in FIG. 1 using cylindrical forming structures 102,103. Both forming structures have an outer diameter of 145 mm and a width of 189 mm. The first forming structure 102 includes parallel continuous grooves 39 and parallel ridges 28 running in a first direction, with center-to-center spacing of about 508 microns in a second direction. The ridges 28 have a taper angle of about 4.4 degrees from vertical. The grooves 39 have a depth of about 1,000 microns and a diameter at half depth of about 340 microns. The second forming structure 103 includes about 287 teeth 26 per square centimeter, with a general shape as shown in FIG. 23A. The teeth 26 are arranged in a rectangular array, with a center-to-center spacing of about 685 microns in a first direction and about 508 microns in a second direction. The teeth 26 have straight, vertical sidewalls in the first direction and tapered inward at an angle of about 4.4 degrees from vertical in the second direction. The teeth 26 have a height of about 1,000 microns and a rectangular cross-section with a first diameter (length) of about 305 microns and a second diameter (width) of about 170 microns at half-height. The tips are rounded with a first radius of about 150 microns and a second radius of about 50 microns. Forming structures 102,103 are machined from aluminum to create grooves; then, forming structure 103 is EDM wire engraved to create teeth 26. The precursor web 50 utilized is a polyethylene film, obtained from Clopay Cincinnati, that is about 25 microns thick and has a basis weight of about 25 grams per square meter (gsm).

The micro-texturing process is performed by feeding the precursor web 50 into the nip 130 of the forming structures 102,103 at a line speed of 8 m/s at room temperature. The precursor web 50 is fed between the forming structures 102,103 in the machine direction (parallel with the grooves 39 and ridges 28). The web strain on the infeed side is about 1% to 5%, i.e., within the linear elastic region of the web. The web strain on the outfeed side should be greater than the infeed strain to keep the web moving. The outfeed wrap angle is 90°. The stripping idler roll 250 is positioned 0.8 mm away from the forming roll 103. The engagement is about 800 microns, at which point the sidewall clearances are about 95 microns in the second direction and the tip to valley clearance is about 200 microns.

Figure 25A:
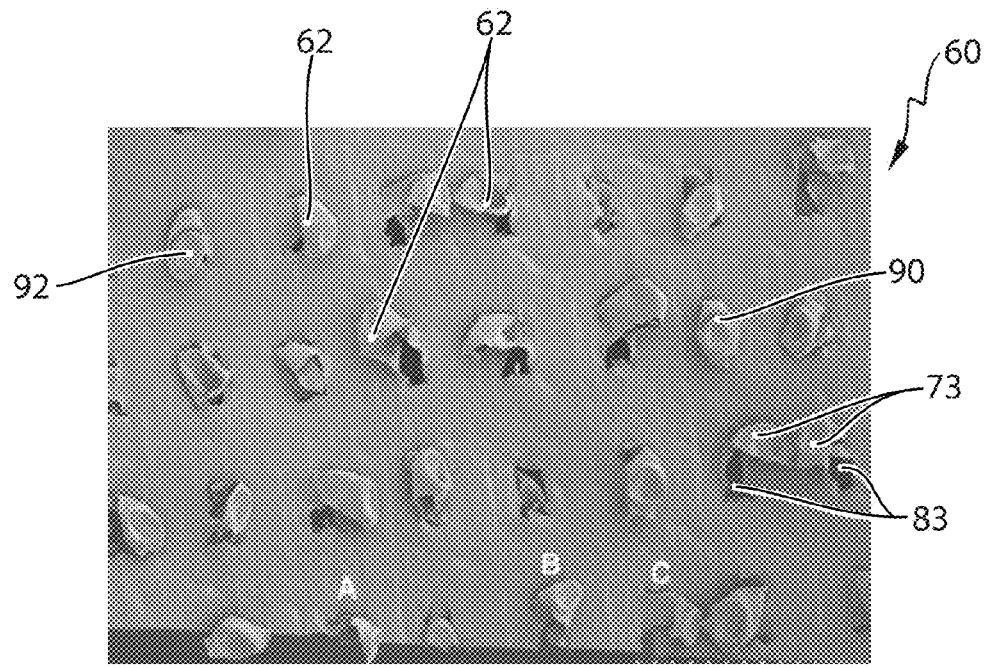
FIGS. 25A and 25B illustrate the micro-textured web of Example 4.
Figure 25B:
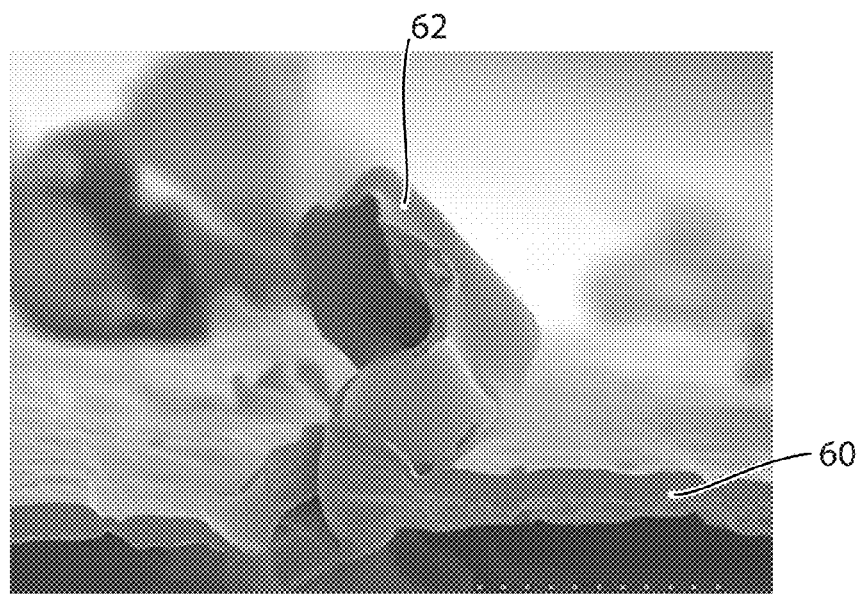

FIGS. 25A and 25B are SEM images which illustrate a resultant micro-textured web 60 which includes a plurality of discrete three-dimensional elements 62. The 3-D elements 62 are in the form of bubbles 90, hoods 92, and chads 73 with significant sidewall and tip thinning. FIG. 25B is a higher magnification cross-section side view of discrete three-dimensional element 62 labeled as A in FIG. 25A.

Example 5

Figure 26A:
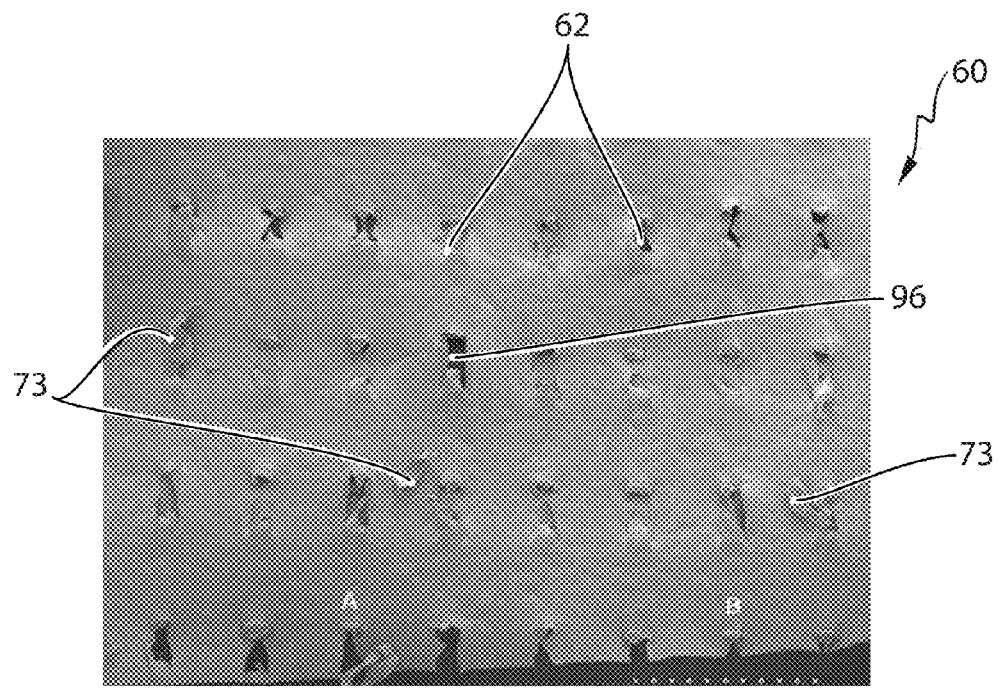
FIGS. 26A and 26B illustrate the micro-textured web of Example 5.
Figure 26B:
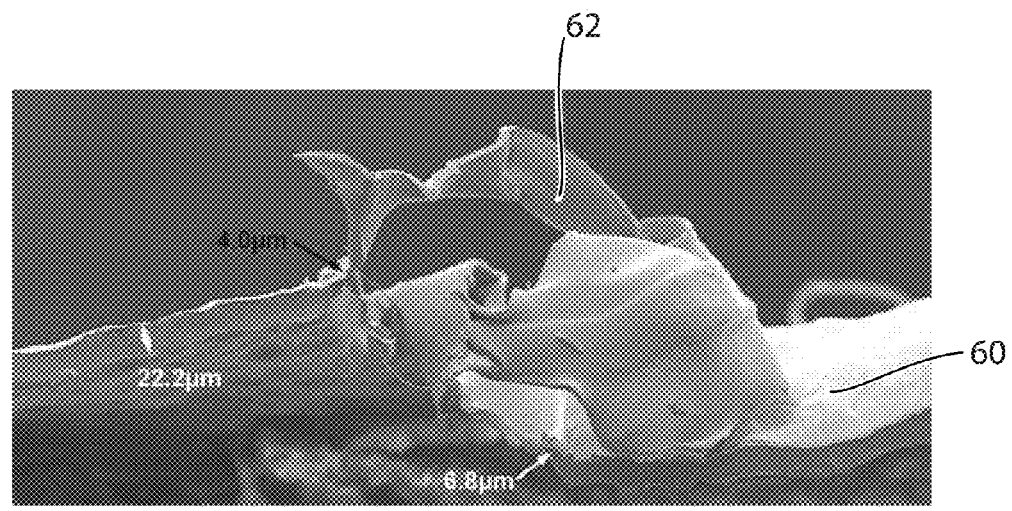

This Example is the same as Example 4, except that both forming structures 102,103 are maintained at 70 degrees Celsius during the process rather than room temperature. FIGS. 26A and 26B are SEM images which illustrate a resultant micro-textured web 60 which includes a plurality of discrete three-dimensional elements 62. The discrete 3-D elements 62 are predominantly in the form of craters 96 and some chads 73 with significant sidewall and tip thinning. FIG. 26B is a higher magnification cross-section side view of discrete three-dimensional element 62 labeled as A in FIG. 26A.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for making a micro-textured web, the process comprising:
   a. providing a precursor web;
   b. providing a first pair of mated forming members including a first forming member and a second forming member forming a first deformation zone therebetween, wherein the first forming member comprises a plurality of protrusions and wherein at least the second forming member comprises a plurality of voids;
   c. moving the precursor web through the first deformation zone, wherein the plurality of voids of the second forming member engage with the plurality of protrusions of the first forming member at an engagement position thereby forming a first plurality of structures on the precursor web;
   d. providing a second pair of mated forming members including a third forming member and a fourth forming member forming a second deformation zone therebetween, wherein the third forming member comprises a second plurality of voids and the fourth forming member comprises a second plurality of protrusions; and
   e. moving the precursor web through the second deformation zone, wherein the second plurality of voids of the third forming member engage with the second plurality of protrusions of the fourth forming member at an engagement position thereby forming a second plurality of structures on the precursor web,
   wherein the first plurality of structures is different than the second plurality of structures, and wherein at least one of the plurality of protrusions and plurality of voids or the second plurality of protrusions and the second plurality of voids are positioned on their respective forming members such that there are between about 200 to about 3000 per square centimeter.

2. The process of claim 1, wherein the first plurality of structures protrude from a first surface of the precursor web.

3. The process of claim 2, wherein the second plurality of structures protrude from a second surface of the precursor web, wherein the second surface is opposite the first surface.

4. The process of claim 1, wherein the first forming member and the second forming member comprise a first plurality of forming elements and a second plurality of forming elements, wherein the first plurality of forming elements and the second plurality of forming elements is different.

5. The process of claim 1, wherein the third forming member and the fourth forming member comprise a first plurality of forming elements and a second plurality of forming elements, wherein the first plurality of forming elements and the second plurality of forming elements is different.

6. The process of claim 1, wherein the precursor web is a film.

7. The process of claim 1, wherein the precursor web is a nonwoven.

8. The process of claim 1, wherein the precursor web is a laminate comprising nonwoven and film.

9. The process of claim 1, wherein the precursor web is a laminate comprising a first nonwoven and a second nonwoven.

10. The process of claim 1, wherein at least a portion of the first plurality of structures comprises a closed end and wherein at least a portion of the second plurality of structures is open.

11. The process of claim 9, wherein at least a portion of the first plurality of structures comprises a closed end and wherein at least a portion of the second plurality of structures is open.

12. The process of claim 11, wherein at least one of the first nonwoven and the second nonwoven comprise contrasting colors.

13. A process for making a disposable absorbent article, the process comprising:
   a. providing a precursor web;
   b. providing a first pair of mated forming members including a first forming member and a second forming member forming a first deformation zone therebetween, wherein the first forming member comprises a plurality of protrusions and wherein at least the second forming member comprises a plurality of voids;
   c. moving the precursor web through the first deformation zone, wherein the plurality of voids of the second forming member engage with the plurality of protrusions of the first forming member at an engagement position thereby forming a first plurality of structures on the precursor web;
   d. providing a second pair of mated forming members including a third forming member and a fourth forming member forming a second deformation zone therebetween, wherein the third forming member comprises a second plurality of voids and the fourth forming member comprises a second plurality of protrusions;

e. moving the precursor web through the second deformation zone, wherein the second plurality of voids of the third forming member engage with the second plurality of protrusions of the fourth forming member at an engagement position thereby forming a second plurality of structures on the precursor web, wherein the first plurality of structures is different than the second plurality of structures, and wherein at least one of the plurality of protrusions and plurality of voids or the second plurality of protrusions and the second plurality of voids are positioned on their respective forming members such that there are between about 200 to about 3000 per square centimeter; and f. utilizing the precursor web as a topsheet for an absorbent article.

14. The process of claim 13, wherein the first plurality of structures protrude from a first surface of the precursor web.

15. The process of claim 14, wherein the second plurality of structures protrude from a second surface of the precursor web, wherein the second surface is opposite the first surface.

16. The process of claim 13, wherein the first forming member and the second forming member comprise a first plurality of forming elements and a second plurality of forming elements, wherein the first plurality of forming elements and the second plurality of forming elements is different.

17. The process of claim 13, wherein the third forming member and the fourth forming member comprise a first plurality of forming elements and a second plurality of forming elements, wherein the first plurality of forming elements and the second plurality of forming elements is different.

18. The process of claim 13, wherein the precursor web is a laminate comprising a first nonwoven and a second nonwoven.

19. The process of claim 13, wherein at least a portion of the first plurality of structures comprises a closed end and wherein at least a portion of the second plurality of structures is open.

20. A process for making a micro-textured web, the process comprising:

a. providing a precursor web;

b. providing a pair of mated forming members including a first forming member and a second forming member forming a first deformation zone therebetween, wherein the first forming member comprises a first plurality of forming elements in a first portion, a second plurality of forming elements in a second portion, and a first plurality of voids in a third portion disposed between the first portion and the second portion, and wherein the second forming member comprises a first plurality of voids in a first portion, a second plurality of voids in a second portion, and a first plurality of forming elements in a third portion disposed between the first portion and second portion; and c. moving the precursor web through the first deformation zone, wherein the first plurality of forming elements of the first forming member engage the first plurality of voids of the second forming member, the second plurality of forming elements of the first forming member engage the second plurality of voids of the second forming member, and wherein the first plurality of forming elements of the second forming member engage the first plurality of voids in the first forming member, thereby forming a first plurality of structures on the precursor web and a second plurality of structures on the precursor web, wherein the first plurality of structures and the second plurality of structures extend in different directions from the precursor web, and wherein at least one of the first plurality of forming elements and first plurality of voids or the second plurality of forming elements and the second plurality of voids are positioned on their respective forming members such that there are between about 200 to about 3000 per square centimeter.

* * * * *